United States Patent
Coe et al.

(10) Patent No.: US 10,022,442 B2
(45) Date of Patent: *Jul. 17, 2018

(54) PYRAZOLOPYRIMIDINE COMPOUNDS

(71) Applicant: GlaxoSmithKline LLC, Philadelphia, PA (US)

(72) Inventors: Diane Mary Coe, Stevenage (GB); Stephen Allan Smith, Stevenage (GB)

(73) Assignee: GLAXOSMITHKLINE LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/497,852

(22) Filed: Apr. 26, 2017

(65) Prior Publication Data

US 2017/0290910 A1    Oct. 12, 2017

Related U.S. Application Data

(63) Continuation of application No. 14/872,620, filed on Oct. 1, 2015, now Pat. No. 9,662,336, which is a continuation of application No. 13/973,466, filed on Aug. 22, 2013, now Pat. No. 9,173,872.

(60) Provisional application No. 61/774,094, filed on Mar. 7, 2013, provisional application No. 61/692,853, filed on Aug. 24, 2012.

(51) Int. Cl.
  *A01N 43/90* (2006.01)
  *A61K 31/519* (2006.01)
  *A61K 39/39* (2006.01)
  *A61K 39/00* (2006.01)

(52) U.S. Cl.
  CPC ............ *A61K 39/39* (2013.01); *A61K 31/519* (2013.01); *A61K 39/00* (2013.01); *A61K 2039/55511* (2013.01)

(58) Field of Classification Search
  CPC .................................................. A61K 31/519
  USPC ...................................................... 514/262.1
  See application file for complete search history.

(56) References Cited

U.S. PATENT DOCUMENTS

| | | | |
|---|---|---|---|
| 5,962,479 | A | 10/1999 | Chen |
| 6,376,501 | B1 | 4/2002 | Isobe et al. |
| 6,552,192 | B1 | 4/2003 | Hanuset et al. |
| 7,125,880 | B1 | 10/2006 | Chen |
| 7,390,890 | B2 | 6/2008 | Furneaux et al. |
| 7,642,350 | B2 | 1/2010 | Pryde |
| 7,977,344 | B2 | 7/2011 | Lazarides et al. |
| 8,067,413 | B2 | 11/2011 | Bonnert et al. |
| 8,067,426 | B2 | 11/2011 | Biggadike et al. |
| 8,563,717 | B2 | 10/2013 | Bazin-Lee et al. |
| 8,575,181 | B2 | 11/2013 | Campos et al. |
| 8,575,340 | B2 | 11/2013 | Bazin-Lee et al. |
| 8,703,754 | B2 | 4/2014 | Gibbon et al. |
| 8,765,772 | B2 | 7/2014 | Biggadike et al. |
| 8,802,684 | B2 | 8/2014 | Bazin-Lee et al. |
| 9,173,872 | B2* | 11/2015 | Coe ............ A61K 31/437 |
| 9,555,036 | B2* | 1/2017 | Coe ............ A61K 31/437 |
| 9,662,336 | B2* | 5/2017 | Coe ............ A61K 31/437 |
| 2001/0020030 | A1 | 9/2001 | Stewart et al. |
| 2002/0037886 | A1 | 3/2002 | Andersson et al. |
| 2003/0187261 | A1 | 10/2003 | Havlicek et al. |
| 2003/0191086 | A1 | 10/2003 | Hanus et al. |
| 2003/0220365 | A1 | 11/2003 | Stewart et al. |

(Continued)

FOREIGN PATENT DOCUMENTS

| | | |
|---|---|---|
| EP | 0773023 A1 | 5/1997 |
| EP | 1043021 A1 | 7/1999 |

(Continued)

OTHER PUBLICATIONS

Akira, S., Toll-like receptors: critical proteins linking innate and acquired immunity, Nat. Immuno. 2001; 2(8); 675-680.
Allergic Rhinitis-Prevention (http://www.webmd.com/allergies/tc/allergic-rhinitis-prevention); WebMD: Allergic Health Center; Jun. 30, 2011.
Asthma Prevention (http://www.webmd.com/asthma/guide/asthma-prevention); WebMD: Asthma Health Center, May 13, 2012.
Berge, S.M., et al. J. Pharmaceutical Science, Published 1977, vol. 66, pp. 1-19.
Borden E.C., et al., Interferons at age 50: past, current and future impact on biomedicine. Nat Rev Drug Discov., Dec. 2007, 6(12), 975-990.

(Continued)

*Primary Examiner* — Jeffrey H Murray
(74) *Attorney, Agent, or Firm* — Leah M. Octavio; Andrea Y. Lochenour

(57) ABSTRACT

Compounds of formula (I) and salts thereof:

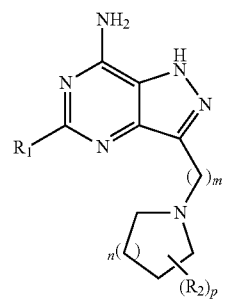

(I)

wherein $R_1$ is n-$C_{1-6}$alkyl or $C_{1-2}$alkoxy$C_{1-2}$alkyl-, $R_2$ is halo, OH or $C_{1-3}$alkyl, m is an integer having a value of 4, 5, 6 or 7, n is an integer having a value of 0, 1, 2 or 3, and p is an integer having a value of 0, 1 or 2, are inducers of human interferon. Compounds which induce human interferon may be useful in the treatment of various disorders, for example the treatment of allergic diseases and other inflammatory conditions, for example allergic rhinitis and asthma, infectious diseases and cancer, and may also be useful as vaccine adjuvants.

16 Claims, 2 Drawing Sheets

(56) References Cited

U.S. PATENT DOCUMENTS

| | | |
|---|---|---|
| 2003/0236216 A1 | 12/2003 | Devos et al. |
| 2004/0029054 A1 | 2/2004 | Vaeth et al. |
| 2004/0063658 A1 | 4/2004 | Roberts et al. |
| 2005/0054590 A1 | 3/2005 | Averett |
| 2006/0029642 A1 | 2/2006 | Miljkovic et al. |
| 2006/0052403 A1 | 3/2006 | Isobe et al. |
| 2006/0148805 A1 | 7/2006 | Chen et al. |
| 2006/0264448 A1 | 11/2006 | Pryde |
| 2007/0190071 A1 | 8/2007 | Kurimoto et al. |
| 2007/0197478 A1 | 8/2007 | Jones et al. |
| 2007/0225303 A1 | 9/2007 | Ogita et al. |
| 2007/0275984 A1 | 11/2007 | Imogai et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0192153 A1 | 7/2009 | Hashimoto et al. |
| 2009/0202484 A1 | 8/2009 | Chong et al. |
| 2009/0233948 A1 | 9/2009 | Evans et al. |
| 2009/0324551 A1 | 12/2009 | Carson et al. |
| 2009/0325877 A1 | 12/2009 | Grunt et al. |
| 2010/0010016 A1 | 1/2010 | Gangjee |
| 2010/0075995 A1 | 3/2010 | Biggadike et al. |
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0240623 A1 | 9/2010 | Cook et al. |
| 2011/0135671 A1 | 6/2011 | Bazin-Lee et al. |
| 2011/0229500 A1 | 9/2011 | Biggadike et al. |
| 2011/0269781 A1 | 11/2011 | Lazarides et al. |
| 2012/0035193 A1 | 2/2012 | Biggadike et al. |
| 2012/0135963 A1 | 5/2012 | Johnson |
| 2012/0171229 A1 | 7/2012 | Zepp et al. |
| 2012/0264768 A1 | 10/2012 | Gangee |
| 2012/0283438 A1 | 11/2012 | Lazarides et al. |
| 2012/0315291 A1 | 12/2012 | Bazin-Lee et al. |
| 2014/0056928 A1 | 2/2014 | Coe et al. |
| 2014/0288099 A1 | 9/2014 | Ambery et al. |
| 2014/0336175 A1 | 11/2014 | Biggadike et al. |
| 2015/0225403 A1 | 8/2015 | Coe et al. |

FOREIGN PATENT DOCUMENTS

| | | |
|---|---|---|
| EP | 1348707 A1 | 10/2003 |
| EP | 1939198 A1 | 3/2007 |
| EP | 1939199 A1 | 7/2008 |
| EP | 2138497 A1 | 12/2009 |
| RU | 2221799 C2 | 1/2004 |
| WO | 9533750 A1 | 12/1995 |
| WO | 9749706 A1 | 12/1997 |
| WO | 1999040091 A1 | 8/1999 |
| WO | 0043394 A1 | 7/2000 |
| WO | 0149688 A1 | 7/2001 |
| WO | 2001083472 A1 | 11/2001 |
| WO | 2003053970 A1 | 7/2003 |
| WO | 2004018496 A1 | 3/2004 |
| WO | 2004029054 A1 | 4/2004 |
| WO | 2005002520 A2 | 1/2005 |
| WO | 2011017611 A1 | 2/2005 |
| WO | 2005020892 A2 | 3/2005 |
| WO | 2005025583 A2 | 3/2005 |
| WO | 2005079195 A2 | 9/2005 |
| WO | 2005097800 A1 | 10/2005 |
| WO | 2005110410 A2 | 11/2005 |
| WO | 2006030031 A1 | 3/2006 |
| WO | 2006117670 A1 | 11/2006 |
| WO | 2007013964 A1 | 2/2007 |
| WO | 2007024944 A1 | 3/2007 |
| WO | 2007028129 A1 | 3/2007 |
| WO | 2007034881 A1 | 3/2007 |
| WO | 2007041863 A1 | 4/2007 |
| WO | 2007093901 A1 | 8/2007 |
| WO | 2007110868 A1 | 10/2007 |
| WO | 2007142755 A2 | 12/2007 |
| WO | 20070138084 A2 | 12/2007 |
| WO | 2008004948 A1 | 1/2008 |
| WO | 2008100457 A2 | 8/2008 |
| WO | 2008101867 A1 | 8/2008 |
| WO | 2008114008 A1 | 9/2008 |
| WO | 2008154221 A2 | 12/2008 |
| WO | 2009019505 A1 | 2/2009 |
| WO | 2009023179 A2 | 2/2009 |
| WO | 2009078798 A1 | 6/2009 |
| WO | 2010006025 A1 | 1/2010 |
| WO | 2010018130 A1 | 2/2010 |
| WO | 2010018131 A1 | 2/2010 |
| WO | 2010018132 A1 | 2/2010 |
| WO | 2010018133 A1 | 2/2010 |
| WO | 2010018134 A1 | 2/2010 |
| WO | 2010083725 A1 | 7/2010 |
| WO | 2011098451 A1 | 8/2011 |
| WO | 2011098452 A1 | 8/2011 |
| WO | 2012009258 A2 | 1/2012 |
| WO | 2012106343 A2 | 8/2012 |
| WO | 2014081643 A1 | 5/2014 |
| WO | 2014081644 A1 | 5/2014 |
| WO | 2014081645 A1 | 5/2014 |
| WO | 2015124591 A1 | 8/2015 |

OTHER PUBLICATIONS

Czarniecki, M. Small Molecule Modulators of Toll-like Receptors, Nov. 13, 2008, vol. 51(21), 6621-6626.

Corren, J., et al.; A Randomized, Controlled, Phase 2 Study of AMG 317, an IL-4Rα Antagonist, in Patients with Asthma; Am. J. Respir. Crit. Care Med.; 2010; vol. 181; pp. 788-796.

Cryz S.J. et al.; Immunotherapy and Vaccines; Ullmann's Encyclopedia of Industrial Chemistry; 2000; vol. 18; pp. 647-722.

Dermer, G.B. Another Anniversary for the War on Cancer. Bio/Technology, 1994, 12, 320.

Freshney, R.I., et al., "Culture of Animal Cells." A Manual of Basic Technique, Alan R. Liss, Inc., 1983, New York, 1-7.

Flood-Page, P. et al.; A Study to Evaluate Safety and Efficacy of Mepolizumab in Patients with Moderate Persistent Asthma; Am. J. Respir. Crit. Care Med.; Dec. 1, 2007; vol. 176, No. 11; pp. 1062-1071.

Gautschi, O., et al. "Aurora Kinases as Anticancer Drug Targets." Clin Cancer Res., Mar. 15, 2008, 14(6), 1639-1648.

Gauvreau, G.M. et al.; Effects of Interleukin-13 Blockade on Allergen-induced Airway Responses in Mild Atopic Asthma; Am. J. Respir. Crit. Care Med.; Nov. 5, 2010; doi:1 0.1164/rccm.201 008-121 OOC.

Golub, T.R., et al. "Molecular Classification of Cancer: Class Discovery and Class Prediction by Gene Expression Monitoring." Science, Oct. 15, 1999, 286, 531-537.

Gould P.L.; Salt Selection for Basic Drugs; International Journal of Pharmaceutics; 1986; 33; 201-217.

Haldar, P., et al., Mepolizumab and Exacerbations of Refractory Eosinophilic Asthma; The New England Journal of Medicine; 2009; vol. 360(10); pp. 973-984.

Hirota, K., et al.; "Discovery of 8-Hydroxyadenines as a Novel Type of Interferon Inducer"; J. Med. Chem.; 2002; vol. 45, No. 25; pp. 5419-5422; American Chemical Society.

Huber, J.P et al.; Culling Edge: Type I IFN Reverses Human Th2 Commitment and Stability by Suppressing GATA3; The Journal of Immunology; 2010; vol. 185; pp. 813-817.

Hussein, W.M., et al. Toll-like receptor agonists: a patent review (2011-2013); Expert Opinion on Therapeutic Patents, Jan. 24, 2014, pp. 1-18.

Isobe, Y., et al.; Synthesis and Biological Evaluation of Novel 9-Substituted-8-hydroxyadenine Derivatives as Potent Interferon Inducers; J. Med. Chem.; 2006; vol. 49, No. 6; pp. 2088-2095; American Chemical Society.

(56) References Cited

OTHER PUBLICATIONS

Kariyawasam, H.H., Et al.; Effects of Anti-IL-13 (Novartis QAX576) on Inflammatory Responses Following Nasal Allergen Challenge (NAC); Am. J. Respir. Crit. Care Med.; 2009; vol. 179; A3642.

Kurimoto, A., et al.; Prodrugs of 9-Benzyl-8-hydroxy-2-(2-hydroxyethylthio)adenine: Potent Interferon Inducing Agents in Monkeys; Chem. Pharm. Bull.; 2004; vol. 52, No. 4; pp. 466-469; Pharmaceutical Society of Japan.

Liu, Y-J., IPC: Profesional Type 1 Interferon-Producing Cells and Plasmacytoid Dendridic Cell Precursors, Ann. Rev. Immunol., 2005; 23:275-306.

Ma, R., Additive effects of CpG ODN and R-848 as adjuvants on augmenting immune responses to HBsAg vaccination, Biochem. Biophys., Res. Commun., 2007; 361:537-542.

McMahon G., et al. VEGF Receptor Signaling in Tumor Angiogenesis, The Oncologist, 2000, 5(Suppl1), pp. 3-10.

Mountzios, G., et al. "Aurora kinases as targets for cancer therapy." Cancer Treatment Reviews, 2008, 34, 175-182.

Pinedo, H.M., et al. Translational Research: The Role of VEGH in Tumor Angiogenesis. The Oncologist, 2000, 5(Suppl1), pp. 1-2.

Pyne, S., et al. "Spingosine Kinase Inhibitors and Cancer: Seeking the Golden Sword of Hercules." Cancer Research, 2011, 71, 6576-6582.

Roemer, T., et al. "Auxiliary factors: a chink in the armor of MRSA resistance to β-lactam antibiotics." Current Opinion in Microbiology, 2013, 16, 538-548.

Simon, H-U., et al.; Clinical and immunological effects of low-dose IFN-α treatment in patients with corticosteroid-resistant asthma; Allergy; 2003; vol. 58; pp. 1250-1255.

Simone, J.V. Cecil Textbook of Medicine, edited by Bennet J.C. and Plum F., 20th edition, vol. 1, 1996, 1004-1010.

Snyder, J.W., et al. "Common bacteria whose susceptibility to antimicrobials is no longer predictable." J. Med. Liban, Pub Med Abstract, 2000, 48(4), 208-214.

Sugar, A.M., et al. "Comparison of Three Methods of Antifungal Susceptibility Testing with the Proposed NCCLS Standard Broth Microdilution Assay: Lack of Phenol Red." Diagno Microbicl Infect Dis, 1995, 21, 129-133.

Swarbrick, J., et al. Encyclopedia of Pharmaceutical Technology, Published 1996, vol. 13, pp. 453-499.

Tao, B., Treatment of allergic airway inflammation and hyper-responsiveness by imiquimod modulating transcription factors T-bet and GATA-3, Chin. Med. J. 2006; 119(8): 640-648.

Turner, W.W., et al. "Recent Advances in the Medicinal Chemistry of Antifungal Agents." Current Pharmaceutical Design, 1996, 2, 209-224.

* cited by examiner

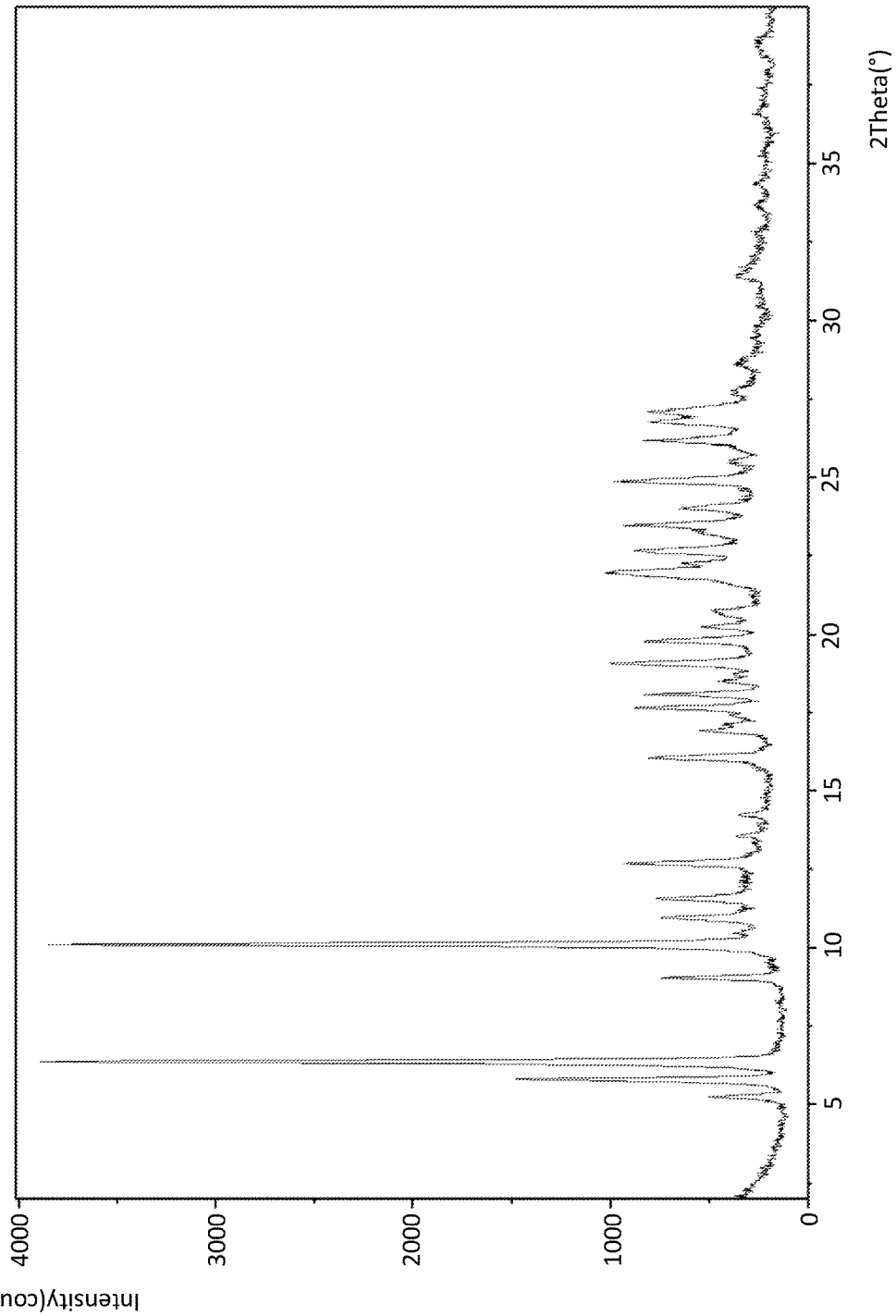
FIG. 1: XRPD Diffractogram of Example 21

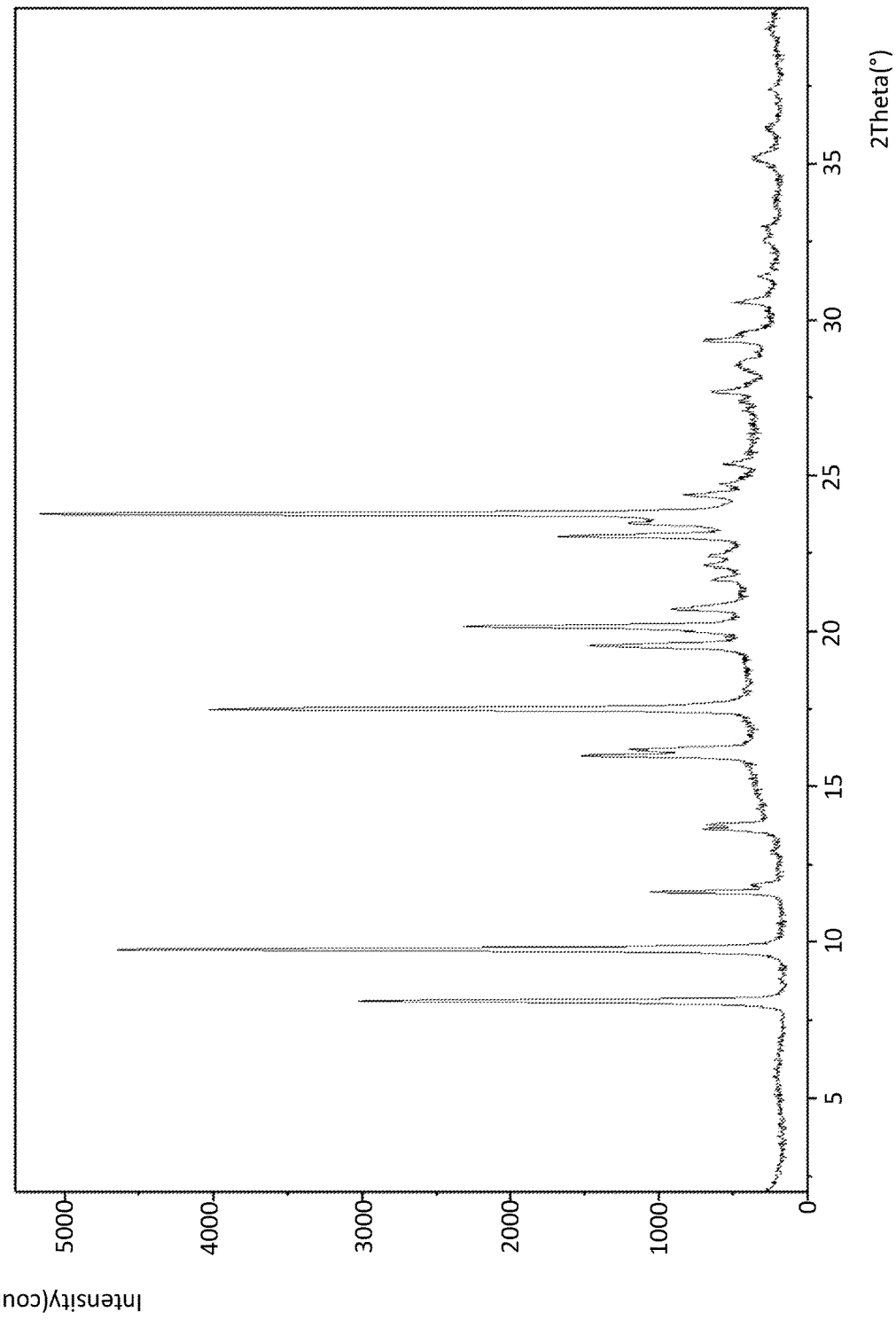
FIG. 2: XRPD Diffractogram of Example 22

PYRAZOLOPYRIMIDINE COMPOUNDS

This Application is a Continuation of U.S. application Ser. No. 14/872,620 filed Oct. 1, 2015, which is a Continuation of U.S. application Ser. No. 13/973,466 filed Aug. 22, 2013 (granted as U.S. Pat. No. 9,173,872 on Nov. 3, 2015), which claims priority from U.S. Provisional 61/744,094 filed Mar. 7, 2013, which claims priority from U.S. Provisional 61/692,853 filed Aug. 24, 2012, all of which are incorporated herein in their entirety.

FIELD OF THE INVENTION

The present invention relates to compounds, processes for their preparation, compositions containing them, to their use in the treatment of various disorders in particular allergic diseases and other inflammatory conditions for example allergic rhinitis and asthma, infectious diseases, and cancer, and as vaccine adjuvants.

BACKGROUND OF THE INVENTION

Vertebrates are constantly threatened by the invasion of microorganisms and have evolved mechanisms of immune defence to eliminate infective pathogens. In mammals, this immune system comprises two branches; innate immunity and acquired immunity. The first line of host defence is the innate immune system, which is mediated by macrophages and dendritic cells. Acquired immunity involves the elimination of pathogens at the late stages of infection and also enables the generation of immunological memory. Acquired immunity is highly specific, due to the vast repertoire of lymphocytes with antigen-specific receptors that have undergone gene rearrangement.

Central to the generation of an effective innate immune response in mammals are mechanisms which bring about the induction of interferons and other cytokines which act upon cells to induce a number of effects. In man, the type I interferons are a family of related proteins encoded by genes on chromosome 9 and encoding at least 13 isoforms of interferon alpha (IFNα) and one isoform of interferon beta (IFNβ). Interferon was first described as a substance which could protect cells from viral infection (Isaacs & Lindemann, *J. Virus Interference. Proc. R. Soc. Lon. Ser. B. Biol. Sci.* 1957: 147, 258-267). Recombinant IFNα was the first approved biological therapeutic and has become an important therapy in viral infections and in cancer. As well as direct antiviral activity on cells, interferons are known to be potent modulators of the immune response, acting on cells of the immune system (Gonzalez-Navajas J. M. et al *Nature Reviews Immunology,* 2012; 2, 125-35).

Toll-like receptors (TLRs) are a family of ten Pattern Recognition Receptors described in man (Gay, N. J. et al, *Annu. Rev. Biochem.,* 2007: 46, 141-165). TLRs are expressed predominantly by innate immune cells where their role is to monitor the environment for signs of infection and, on activation, mobilise defence mechanisms aimed at the elimination of invading pathogens. The early innate immune-responses triggered by TLRs limit the spread of infection, while the pro-inflammatory cytokines and chemokines that they induce lead to recruitment and activation of antigen presenting cells, B cells, and T cells. The TLRs can modulate the nature of the adaptive immune-responses to give appropriate protection via dendritic cell-activation and cytokine release (Akira S. et al, Nat. Immunol., 2001: 2, 675-680). The profile of the response seen from different TLR agonists depends on the cell type activated.

TLR7 is a member of the subgroup of TLRs (TLRs 3, 7, 8, and 9), localised in the endosomal compartment of cells which have become specialised to detect non-self nucleic acids. TLR7 plays a key role in anti-viral defence via the recognition of ssRNA (Diebold S. S. et al, *Science,* 2004: 303, 1529-1531; and Lund J. M. et al, *PNAS,* 2004: 101, 5598-5603). TLR7 has a restricted expression-profile in man and is expressed predominantly by B cells and plasmacytoid dendritic cells (pDC), and to a lesser extent by monocytes. Plasmacytoid DCs are a unique population of lymphoid-derived dendritic cells (0.2-0.8% of Peripheral Blood Mononuclear Cells (PBMCs)) which are the primary type I interferon-producing cells secreting high levels of interferon-alpha (IFNα) and interferon-beta (IFNβ) in response to viral infections (Liu Y-J, *Annu. Rev. Immunol.,* 2005: 23, 275-306).

Administration of a small molecule compound which could stimulate the innate immune response, including the activation of type I interferons and other cytokines via Toll-like receptors, could become an important strategy for the treatment or prevention of human diseases. Small molecule agonists of TLR7 have been described which can induce interferon alpha in animals and in man (Takeda K. et al, *Annu. Rev. Immunol.,* 2003: 21, 335-76). TLR7 agonists include imidazoquinoline compounds such as imiquimod and resiquimod, oxoadenine analogues and also nucleoside analogues such as loxoribine and 7-thia-8-oxoguanosine which have long been known to induce interferon alpha (Czarniecki. M., *J. Med, Chem.,* 2008: 51, 6621-6626; Hedayat M. et al, *Medicinal Research Reviews,* 2012: 32, 294-325). This type of immunomodulatory strategy has the potential to identify compounds which may be useful in the treatment of allergic diseases (Moisan J. et al, *Am. J. Physiol. Lung Cell Mol. Physiol.,* 2006: 290, L987-995), viral infections (Horcroft N. J. et al, *J. Antimicrob. Chemther,* 2012: 67, 789-801), cancer (Krieg A., *Curr. Oncol. Rep.,* 2004: 6(2), 88-95), other inflammatory conditions such as irritable bowel disease (Rakoff-Nahoum S., *Cell.,* 2004, 23, 118(2): 229-41), and as vaccine adjuvants (Persing et al. *Trends Microbiol.* 2002: 10(10 Suppl), S32-7).

More specifically, allergic diseases are associated with a Th2-biased immune-response to allergens. Th2 responses are associated with raised levels of IgE, which, via its effects on mast cells, promotes a hypersensitivity to allergens, resulting in the symptoms seen, for example, in asthma and allergic rhinitis. In healthy individuals the immune-response to allergens is more balanced with a mixed Th2/Th1 and regulatory T cell response. TLR7 ligands have been shown to reduce Th2 cytokine and enhance Th1 cytokine release in vitro and to ameliorate Th2-type inflammatory responses in allergic lung models in vivo (Duechs M. J., *Pulmonary Pharmacology & Therapeutics,* 2011: 24, 203-214; Fili L. et al, *J. All. Clin. Immunol.,* 2006: 118, 511-517; Tao et al, *Chin. Med. J.,* 2006: 119, 640-648; Van L. P. *Eur. J. Immunol.,* 2011: 41, 1992-1999). Thus TLR7 ligands have the potential to rebalance the immune-response seen in allergic individuals and lead to disease modification. Recent clinical studies with the TLR7 agonist have shown repeated intranasal stimulation of TLR7 to produce a sustained reduction in the responsiveness to allergen in patients with both allergic rhinitis and allergic asthma (Greiff L. *Respiratory Research,* 2012: 13, 53; Leaker B. R. et al, *Am. J. Respir. Crit. Care Med.,* 2012: 185, A4184).

In the search for novel small molecule inducers of human interferon IFNα an assay strategy has been developed to characterise small molecule (regardless of mechanism) which is based on stimulation of primary human donor cells or whole blood with compounds, and is disclosed herein.

SUMMARY OF THE INVENTION

In a first aspect, the present invention is directed to compounds of formula (I) and salts thereof:

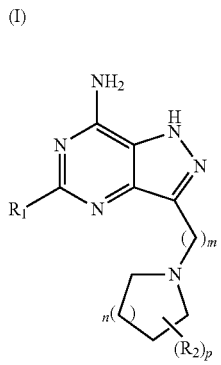

(I)

wherein:
$R_1$ is n-$C_{1-6}$alkyl or $C_{1-2}$alkoxy$C_{1-2}$alkyl-;
$R_2$ is halo, hydroxy or $C_{1-3}$alkyl;
m is an integer having a value of 4 to 7;
n is an integer having a value of 0 to 3;
p is an integer having a value of 0 to 2.

Certain compounds of the invention have been shown to be inducers of human interferon and may possess a desirable developability profile compared to known inducers of human interferon. In addition, certain compounds of the invention may also show selectivity for IFNα with respect to TNFα. Compounds which induce human interferon may be useful in the treatment of various disorders, for example the treatment of allergic diseases and other inflammatory conditions, for example allergic rhinitis and asthma, the treatment of infectious diseases and cancer. Accordingly, the invention is further directed to pharmaceutical compositions comprising a compound of formula (I), or a pharmaceutically acceptable salt thereof. The present invention is further directed to methods of treatments of disorders associated therewith using a compound of formula (I) or a pharmaceutically acceptable salt thereof, or a pharmaceutical composition comprising a compound of formula (I) or a pharmaceutically acceptable salt thereof.

The compounds of the invention may also have use as vaccine adjuvants. Consequently, the present invention is further directed to a vaccine composition comprising a compound of formula (I), or a pharmaceutically acceptable salt thereof, and an antigen or antigen composition.

Certain compounds of the invention are potent immunomodulators and accordingly, care should be exercised in their handling.

BRIEF DESCRIPTION OF THE SEVERAL VIEWS OF THE DRAWINGS

FIG. 1 illustrates the XRPD diffractogram of Example 21.
FIG. 2 illustrates the XRPD diffractogram of Example 22.

DETAILED DESCRIPTION OF THE INVENTION

In a first aspect, the present invention is directed to compounds of formula (I) and salts thereof:

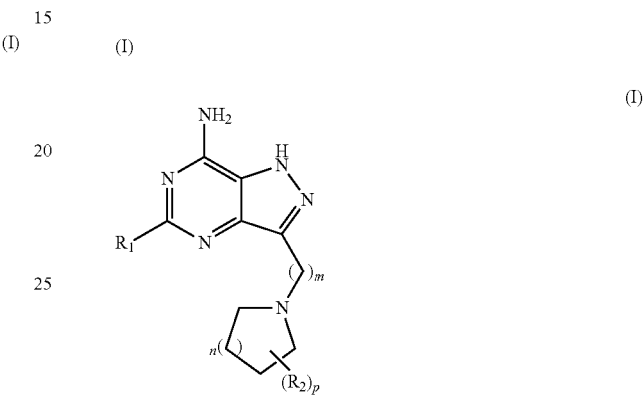

(I)

wherein:
$R_1$ is n-$C_{1-6}$alkyl or $C_{1-2}$alkoxy$C_{1-2}$alkyl-;
$R_2$ is halo, hydroxy or $C_{1-3}$alkyl;
m is an integer having a value of 4 to 7;
n is an integer having a value of 0 to 3;
p is an integer having a value of 0 to 2.

In a further aspect, the present invention is directed to compounds of formula (I) and salts thereof:

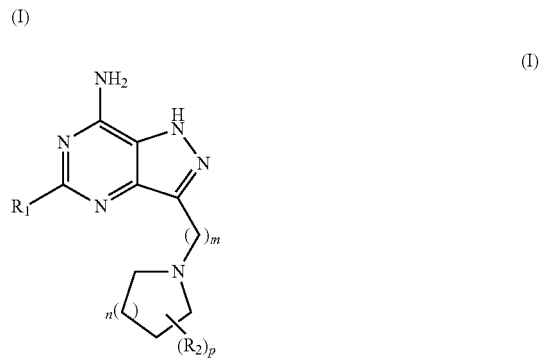

(I)

wherein:
$R_1$ is n-$C_{3-6}$alkyl or $C_{1-2}$alkoxy$C_{1-2}$alkyl-;
each $R_2$ independently represents halo, OH or $C_{1-3}$alkyl;
m is an integer having a value of 4, 5, 6 or 7;
n is an integer having a value of 0, 1, 2 or 3;
p is an integer having a value of 0, 1 or 2.

In a further aspect, the present invention is directed to compounds of formula (I) and salts thereof:

(I)

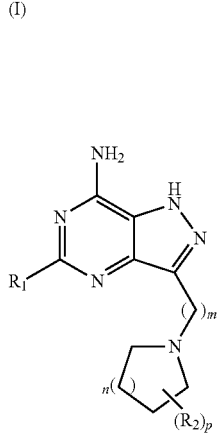

wherein:
R₁ is n-C₄₋₆alkyl;
R₂ is halo or OH;
m is an integer having a value of 5, 6 or 7;
n is an integer having a value of 1, 2 or 3;
p is an integer having a value of 0 or 1.

In a further aspect, the present invention is directed to compounds of formula (I) and salts thereof:

(I)

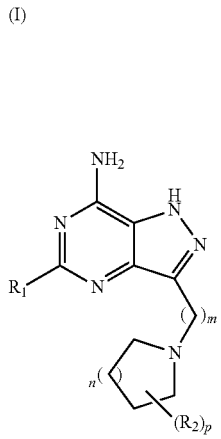

wherein:
R₁ is n-butyl or 2-methoxyethyl;
R₂ is halo or OH;
m is an integer having a value of 5, 6 or 7;
n is an integer having a value of 1, 2 or 3;
p is an integer having a value of 0 or 1.

In a further aspect, the present invention is directed to compounds of formula (I) and salts thereof:

(I)

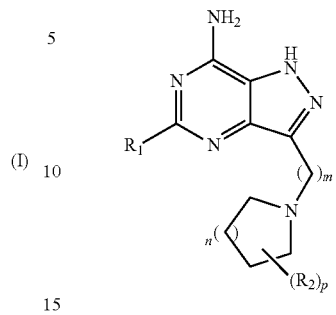

wherein:
R₁ is n-butyl or 2-methoxyethyl;
R₂ is F or OH;
m is an integer having a value of 5, 6 or 7;
n is an integer having a value of 1, 2 or 3;
p is an integer having a value of 0 or 1.

In a further aspect, the present invention is directed to compounds of formula (I) and salts thereof:

(I)

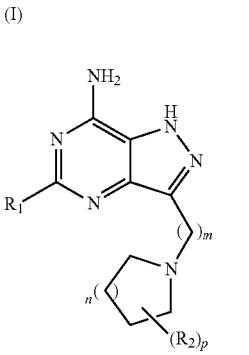

wherein:
R₁ is n-butyl or 2-methoxyethyl;
m is an integer having a value of 5, 6 or 7;
n is an integer having a value of 1, 2 or 3;
p is 0.

In a further aspect, R₁ is n-C₄₋₆alkyl, for example n-butyl.
In a further aspect, R, is 2-methoxyethyl.
In a further aspect, m is an integer having a value of 5 or 6.
In a further aspect, n is 1 or 2.
In a further aspect, p is 0 or 1.
In a further aspect, R₂ is halo or OH.
In a further aspect, R₂ is F or OH.

Examples of compounds of formula (I) are provided in the following group, and form a further aspect of the invention:
5-Butyl-3-(6-(piperidin-1-yl)hexyl)-1H-pyrazolo[4,3-d]pyrimidin-7-amine;
5-(2-Methoxyethyl)-3-(6-(piperidin-1-yl)hexyl)-1H-pyrazolo[4,3-d]pyrimidin-7-amine;
5-Butyl-3-(6-(pyrrolidin-1-yl)hexyl)-1H-pyrazolo[4,3-d]pyrimidin-7-amine;
5-(2-Methoxyethyl)-3-(6-(pyrrolidin-1-yl)hexyl)-1H-pyrazolo[4,3-d]pyrimidin-7-amine;
5-Butyl-3-(5-(piperidin-1-yl)pentyl)-1H-pyrazolo[4,3-d]pyrimidin-7-amine;
5-Butyl-3-(5-(pyrrolidin-1-yl)pentyl)-1H-pyrazolo[4,3-d]pyrimidin-7-amine;

5-Butyl-3-(7-(piperidin-1-yl)heptyl)-1H-pyrazolo[4,3-d]pyrimidin-7-amine;
5-Butyl-3-(7-(pyrrolidin-1-yl)heptyl)-1H-pyrazolo[4,3-d]pyrimidin-7-amine;
3-(6-(Azepan-1-yl)hexyl)-5-butyl-1H-pyrazolo[4,3-d]pyrimidin-7-amine;
3-(5-(Azepan-1-yl)pentyl)-5-butyl-1H-pyrazolo[4,3-d]pyrimidin-7-amine;
(S)-5-Butyl-3-(6-(3-fluoropyrrolidin-1-yl)hexyl)-1H-pyrazolo[4,3-d]pyrimidin-7-amine;
(S)-5-Butyl-3-(5-(3-fluoropyrrolidin-1-yl)pentyl)-1H-pyrazolo[4,3-d]pyrimidin-7-amine;
(R)-5-Butyl-3-(6-(3-fluoropyrrolidin-1-yl)hexyl)-1H-pyrazolo[4,3-d]pyrimidin-7-amine;
(R)-5-Butyl-3-(5-(3-fluoropyrrolidin-1-yl)pentyl)-1H-pyrazolo[4,3-d]pyrimidin-7-amine;
1-(6-(7-Amino-5-butyl-1H-pyrazolo[4,3-d]pyrimidin-3-yl)hexyl)piperidin-4-ol;
1-(5-(7-Amino-5-butyl-1H-pyrazolo[4,3-d]pyrimidin-3-yl)pentyl) piperidin-4-ol;
5-Butyl-3-(6-(4-fluoropiperidin-1-yl)hexyl)-1H-pyrazolo[4,3-d]pyrimidin-7-amine;
5-Butyl-3-(5-(4-fluoropiperidin-1-yl)pentyl)-1H-pyrazolo[4,3-d]pyrimidin-7-amine, and salts thereof.

In a further aspect, the present invention is directed to 5-Butyl-3-(6-(pyrrolidin-1-yl)hexyl)-1H-pyrazolo[4,3-d]pyrimidin-7-amine, or a salt thereof.

As used herein, the term "alkyl" refers to a saturated, hydrocarbon chain having the specified number of member atoms. Unless otherwise stated, the term 'alkyl' includes straight and branched alkyl groups. For example, $C_{1-6}$alkyl refers to a saturated, straight or branched hydrocarbon chain having from 1 to 6 carbon atoms, such as ethyl and isopropyl, and n-$C_{1-6}$alkyl refers to a saturated, straight hydrocarbon chain having from 1 to 6 carbon atoms, such as n-propyl, and n-butyl.

It is to be understood that references herein to compounds of the invention mean a compound of formula (I) as the free base, or as a salt, for example a pharmaceutically acceptable salt.

In one aspect of the invention, a compound of formula (I) is in the form of a free base.

Salts of the compounds of formula (I) include pharmaceutically acceptable salts and salts which may not be pharmaceutically acceptable but may be useful in the preparation of compounds of formula (I) and pharmaceutically acceptable salts thereof.

In one aspect of the invention, a compound of formula (I) is in the form of a pharmaceutically acceptable salt.

Salts may be derived from certain inorganic or organic acids.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively. Furthermore, pharmaceutically-acceptable salts of the compound of formula (I) may be prepared during further processing of the free acid or base form, for example in situ during manufacture into a pharmaceutical formulation.

Examples of salts are pharmaceutically acceptable salts. Pharmaceutically acceptable salts include acid addition salts. For a review on suitable salts see Berge et al., *J. Pharm. Sci.*, 66:1-19 (1977).

Examples of pharmaceutically acceptable acid addition salts of a compound of formula (I) include inorganic acids such as, for example, hydrochloric acid, hydrobromic acid, orthophosphoric acid, nitric acid, phosphoric acid, or sulphuric acid, or with organic acids such as, for example, methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesuphonic, hexanoic acid or acetylsalicylic acid.

The invention includes within its scope all possible stoichiometric and non-stoichiometric forms of the salts of the compounds of formula (I). For example, a dimaleate or hemi-succinate salt of the compound of formula (I).

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable acid (such as hydrobromic, hydrochloric, sulphuric, maleic, p-toluenesulphonic, methanesulphonic, naphthalenesulphonic or succinic acids), optionally in a suitable solvent such as an organic solvent, to give the salt which is usually isolated for example by crystallisation and filtration.

Examples of pharmaceutically acceptable salts of 5-Butyl-3-(6-(pyrrolidin-1-yl)hexyl)-1H-pyrazolo[4,3-d]pyrimidin-7-amine are the maleate, dimaleate, and hemi-succinate salts.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis. Solvates of the compounds of formula (I) are within the scope of the invention. As used herein, the term solvate encompasses solvates of both a free base compound as well as any salt thereof.

Certain of the compounds of the invention may exist in tautomeric forms. It will be understood that the present invention encompasses all of the tautomers of the compounds of the invention whether as individual tautomers or as mixtures thereof.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

In a further aspect, the present invention is directed to a crystalline solid state form of 5-Butyl-3-(6-(pyrrolidin-1-yl)hexyl)-1H-pyrazolo[4,3-d]pyrimidin-7-amine dimaleate, characterised by an X-ray powder diffraction pattern having diffraction peaks at 2θ values of 5.3, 5.8, 6.4, 9.0, 10.1, 10.9, 11.6, 12.7, 16.0 and 19.1.

In a further aspect, the present invention is directed to a crystalline solid state form of 5-Butyl-3-(6-(pyrrolidin-1-yl)hexyl)-1H-pyrazolo[4,3-d]pyrimidin-7-amine hemi-succinate, characterised by an X-ray powder diffraction pattern having diffraction peaks at 2θ values of 8.1, 9.8, 11.6, 16.0, 17.5, 19.5, 20.2, 23.0 and 23.7.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

The present invention also includes all suitable isotopic variations of a compound of formula (I) or a pharmaceutically acceptable salt thereof. An isotopic variation of a compound of formula (I), or a pharmaceutically acceptable salt thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2H$, $^3H$, $^{13}C$, $^{14}C$, $^{15}N$, $^{17}O$, $^{18}O$, $^{18}F$ and $^{36}Cl$, respectively. Certain isotopic variations of a compound of formula (I) or a salt or solvate thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of a compound of formula (I), or a pharmaceutically salt thereof, can generally be prepared by conventional procedures such as by the illustrative methods or by the preparations described in the Examples hereafter using appropriate isotopic variations of suitable reagents.

It will be appreciated from the foregoing that included within the scope of the invention are solvates, hydrates, isomers, isotopic variations and polymorphic forms of the compounds of formula (I) and salts and solvates thereof.

Compound Preparation

The compounds of formula (I) and salts thereof may be prepared by the methodology described hereinafter, constituting further aspects of this invention.

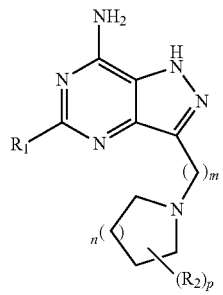

(I)

Accordingly, there is provided a process for the preparation of a compound of formula (I), which process comprises the functional group interconversion or deprotection of a compound of formula (II):

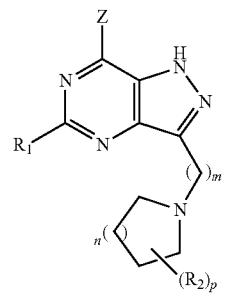

(II)

wherein $R_1$, $R_2$, m, n and p are as defined hereinbefore for a compound of formula (I) and Z is OH or amino substituted with a suitable protecting group such as 3, 4-dimethoxybenzyl or 2,4-dimethoxybenzyl and thereafter, if required, preparing a salt of the compound so-formed.

For example when Z is OH, a compound of formula (II) is dissolved in phosphorus oxychloride and heated, at a suitable temperature, for example 120° C. for a suitable period, for example 45-120 minutes. The reaction mixture is evaporated and azeotroped with a suitable solvent, for example toluene. A solution of aqueous ammonia (0.88) is then added to a solution of the material in a suitable solvent, for example iso-propyl alcohol. The resultant mixture is then heated in a microwave heater at a suitable temperature, for example 120-150° C. for a suitable period of time, for example 1-2 hours. The product (I) is isolated by removal of the solvent and purification if required.

For example when Z is a (3,4-dimethoxyphenyl)methanamine group, a compound of formula (II) is treated with a suitable acid such as trifluoroacetic acid and heated at a suitable temperature, for example 120° C., in a microwave heater for a suitable period of time, for example 4 hours. The product (I) is isolated by removal of the solvent, aqueous work up and purification if required.

For example when Z is a (2,4-dimethoxyphenyl)methanamine group, a compound of formula (II) is treated with a suitable acid such as trifluoroacetic acid and heated at a suitable temperature, for example 60° C. for a suitable period of time, for example 2.5-4 hours. The product (I) is isolated by the removal of solvent, aqueous work-up and purification if required.

A compound of formula (II) may be prepared by reaction of a compound of formula (III):

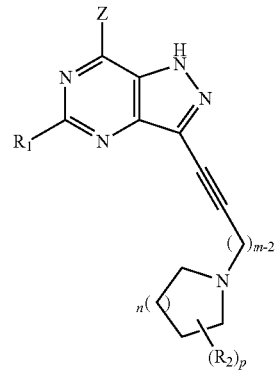

(III)

wherein $R_1$, $R_2$, m, n and p are as hereinbefore defined for a compound of formula (I) and Z is as hereinbefore defined for a compound of formula (II), with hydrogen in the presence of a catalyst.

For example a compound of formula (III) is dissolved in a suitable solvent for example ethyl alcohol, and passed over a suitable catalyst, for example 10% palladium on carbon, in the presence of hydrogen at a suitable temperature, for example 20-60° C., in a suitable flow hydrogenation apparatus such as the Thales H-Cube™. Alternatively a compound of formula (III) is dissolved in a suitable solvent for example ethyl alcohol and stirred under an atmosphere of hydrogen in the presence of a suitable catalyst, for example 10% palladium on carbon, at a suitable temperature, for example 20° C., for a suitable period of time 2-18 hours. The product (II) is isolated by removal of the solvent, aqueous work up and purification if required.

A compound of formula (III) may be prepared by reaction of a compound of formula (IV):

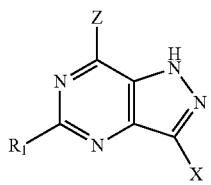

(IV)

wherein $R_1$ is as hereinbefore defined for a compound of formula (I), Z is as hereinbefore defined for a compound of formula (II) and X is a halogen, such as iodine or bromine, with a compound of formula (V):

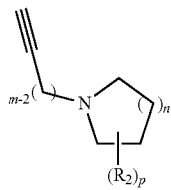

(V)

wherein $R_2$, m, n and p are defined for a compound of formula (I).

For example a compound of formula (IV), is dissolved in a suitable solvent, for example N,N-dimethylformamide, in the presence of copper(I) iodide, a suitable catalyst, for example bis(triphenylphosphine)palladium(II) dichloride and a suitable base, for example triethylamine. A solution of a compound of formula (V) in a suitable solvent, such as N,N-dimethylformamide, is added and the mixture stirred at a suitable temperature, for example 20-55° C. for a suitable period of time, for example 0.5-17 hours. The product (III) is isolated after an aqueous work-up and purification.

A compound of formula (V) may be prepared by reaction of a compound of formula (VI):

(VI)

wherein m is defined for a compound of formula (I) and Y is a leaving group such as a halogen, for example chlorine, bromine or iodine, or an alkyl sulfonate, for example p-toluenesulfonate, with a compound of formula (VII):

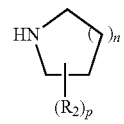

(VII)

wherein $R_2$, n and p are as defined for a compound of formula (I).

For example a compound of formula (VI), a compound of formula (VII) and a suitable base, for example sodium hydrogen carbonate, are dissolved in a suitable solvent, for example N,N-dimethylformamide, and heated at a suitable temperature, for example 80-100° C. for a suitable period of time, for example 16-18 hours. The product (V) is isolated after aqueous work-up and purification, for example by isolation of a suitable crystalline salt, for example the oxalate salt.

Alternatively a compound of formula (III) may be prepared by reaction of a compound of formula (VIII):

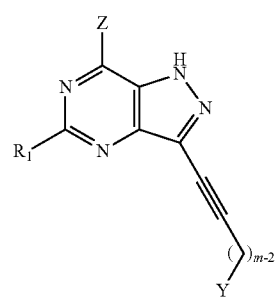

(VIII)

wherein $R_1$ and m are as hereinbefore defined for a compound of formula (I), Z is as hereinbefore defined for a compound of formula (II) and Y is a leaving group as defined for compounds of formula (VI), with a compound of formula (VII) wherein $R_2$, n and p are as defined for a compound of formula (I).

For example a compound of formula (VIII), a compound of formula (VII) and a suitable base, for example triethylamine, are dissolved in a suitable solvent, for example acetonitrile and heated at a suitable temperature, for example 60-80° C. for a suitable period of time, for example 16-26 hours. The product (III) is isolated after an aqueous work-up and purification.

Compounds of formula (VIII) can be prepared by reaction of compounds of formula (IV) with compounds of formula (VI). For example, a compound of formula (IV) is dissolved in a suitable solvent, for example N,N-dimethylformamide, in the presence of copper(I) iodide, a suitable catalyst, for example bis(triphenylphosphine)palladium(II) dichloride and a suitable base, for example triethylamine. A solution of a compound of formula (VI) in a suitable solvent, such as N,N-dimethylformamide, is added and the mixture is stirred at a suitable temperature, for example 20-60° C. for a suitable period of time, for example 2-18 hours. The product (VIII) is isolated after an aqueous work-up and purification.

Alternatively a compound of formula (II) may be prepared by reaction of compounds of formula (IX):

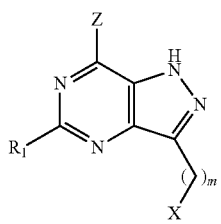

(IX)

wherein $R_1$ and m are as hereinbefore defined for a compound of formula (I), Z is as hereinbefore defined for a compound of formula (II) and X is a leaving group such as a halogen, for example chloro, bromo or iodo, with a compound of formula (VII) wherein $R_2$, n and p are as defined for a compound of formula (I).

For example a mixture of compound of formula (IX), a compound of formula (VII) and a suitable base, for example triethylamine, in a suitable solvent, for example acetonitrile, is stirred at a suitable temperature, for example 20° C., for a suitable period of time, for example 17-19 hours. The product (IX) is isolated after an aqueous work-up and purification.

Compounds of formula (IX) may be prepared by the reaction of compounds of formula (X):

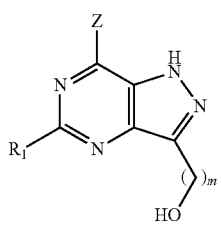

(X)

wherein $R_1$ and m are as hereinbefore defined for a compound of formula (I), Z is as hereinbefore defined for a compound of formula (II) with a suitable halogenating reagent.

For example a solution of triphenylphosphine in a solvent, for example dichloromethane, in added to a mixture of compound of formula (X) and carbon tetrabromide in a suitable solvent, for example, dichloromethane. The reaction is stirred as a suitable temperature, for example 20° C., for a suitable period of time, 18-20 hours. The product (X) is isolated after an aqueous work-up and purification.

Compounds of formula (X) may be prepared by reaction of compounds of formula (XI):

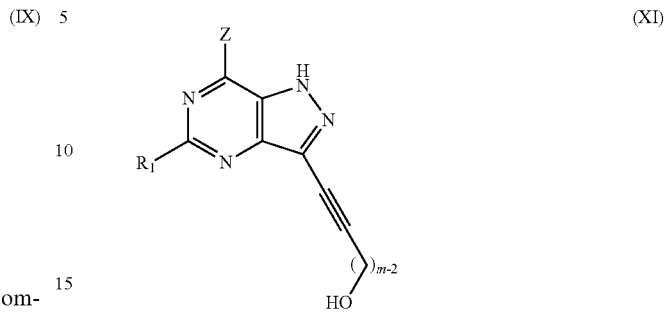

(XI)

wherein $R_1$ and m are as hereinbefore defined for a compound of formula (I), Z is as hereinbefore defined for a compound of formula (II) with hydrogen in the presence of a catalyst.

For example a compound of formula (XI) is dissolved in a suitable solvent, for example ethanol, and stirred under an atmosphere of hydrogen in the presence of a suitable catalyst, for example 10% palladium on carbon, for a suitable period of time, for example 22 hours. The product (XIV) is isolated by removal of the solvent and purification if required.

Compounds of formula (XI) can be prepared by reaction of compounds of formula (IV) with appropriate alkyn-1-ols. For example, a compound of formula (IV) is dissolved in a suitable solvent, for example N,N-dimethylformamide, in the presence of copper(I) iodide, a suitable catalyst, for example bis(triphenylphosphine)palladium(II) dichloride and a suitable base, for example triethylamine. A solution of the alkyn-1-ol in a suitable solvent, such as N,N-dimethylformamide, is added and the mixture is stirred at a suitable temperature, for example 60° C. for a suitable period of time, for example 2-4 hours. The product (XI) is isolated after an aqueous work-up and purification.

Compounds of formula (IV) wherein Z is an amino substituted with a suitable protecting group can be prepared from compounds of formula (IV) wherein Z is an OH group. For example a compound of formula (IV) Z=OH is dissolved in a suitable solvent, for example N,N-dimethylformamide, in the presence of a suitable coupling agent, for example (benzotriazol-1-yloxy)tris(dimethylamino)phosphonium hexafluorophosphate, and a base, for example, 1,8-diazabicyclo[5.4.0]undec-7-ene, is treated with a suitable amine, for example, (3,4-dimethoxyphenyl)methanamine.

The reaction is stirred as a suitable temperature, for example 40° C., for a suitable period of time, for example 3 hours. The product (IV) where Z is (3,4-dimethoxyphenyl)methanamine is isolated after an aqueous work-up and purification.

Alternatively a compound of formula (IV) Z=OH is dissolved in a suitable solvent, for example acetonitrile, in the presence of a suitable coupling agent, for example ((1H-benzo[d][1,2,3]triazol-1-yl)oxy)tri(pyrrolidin-1-yl) phosphonium hexafluorophosphate(V), and a base, for example, 1,8-diazabicyclo[5.4.0]undec-7-ene, is treated with a suitable amine, for example, (2,4-dimethoxyphenyl)methanamine. The reaction is stirred at a suitable temperature, for example 20° C., for a suitable period of time, for example 6 hours. The product (IV) where Z is (3,4-dimethoxyphenyl)methanamine is isolated after separation from the by-products by filtration and purification.

Compounds of formula (IV) wherein Z is an OH group may be prepared by reaction of compounds of formula (XII):

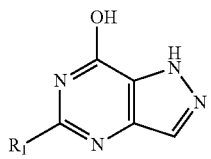

(XII)

wherein $R_1$ as hereinbefore defined for a compound of formula (I), with a halogenating reagent, for example N-iodosuccinimide.

For example, a compound of formula (XII) is dissolved in a suitable solvent, for example N,N-dimethylformamide, and reacted with N-iodosuccinimide at a suitable temperature, for example 60° C. for a suitable period of time, for example 1-2 hours. The product (XII) is isolated after an aqueous work-up and purification.

Compounds of formula (XII) may be prepared by reaction of compounds of formula (XIII):

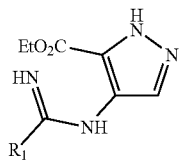

(XIII)

wherein $R_1$ as hereinbefore defined for a compound of formula (I) with a suitable base, for example sodium hydroxide.

A solution of compounds of formula (XIII) in a suitable solvent, for example ethyl alcohol, is treated with an aqueous solution of sodium hydroxide and the reaction mixture stirred at a suitable temperature, for example 80-100° C. for a suitable period of time, for example 1-4 hours. The product (XII) is isolated after an aqueous work-up and purification.

Compounds of formula (XIII) can be prepared by reaction of compounds of formula (XIV):

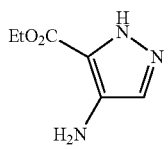

(XIV)

with compounds of formula (XII):

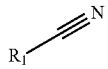

(XV)

wherein $R_1$ is as hereinbefore defined for a compound of formula (I).

For example a mixture of a compound of formula (XIV) and a compound of formula (XV) is treated with a solution of hydrogen chloride in a suitable solvent, for example a solution of hydrogen chloride in 1,4-dioxane and is heated at a suitable temperature, 60-80° C. for a suitable period of time, for example 16-24 hours. The product (XIII) is isolated after evaporation of the solvent.

Compounds of formulae (VI), (VII), (XIV) and (XV) are either known in the literature or are commercially available, for example from Sigma-Aldrich, UK, or may be prepared by analogy with known procedures, for example those disclosed in standard reference texts of synthetic methodology such as J. March, *Advanced Organic Chemistry*, 6th Edition (2007), WileyBlackwell, or *Comprehensive Organic Synthesis* (Trost B. M. and Fleming I., (Eds.), Pergamon Press, 1991), each incorporated herein by reference as it relates to such procedures.

Examples of other protecting groups that may be employed in the synthetic routes described herein and the means for their removal can be found in T. W. Greene '*Protective Groups in Organic Synthesis*', 4th Edition, J. Wiley and Sons, 2006, incorporated herein by reference as it relates to such procedures.

For any of the hereinbefore described reactions or processes, conventional methods of heating and cooling may be employed, for example temperature-regulated oil-baths or temperature-regulated hot-blocks, and ice/salt baths or dry ice/acetone baths respectively. Conventional methods of isolation, for example extraction from or into aqueous or non-aqueous solvents may be used. Conventional methods of drying organic solvents, solutions, or extracts, such as shaking with anhydrous magnesium sulphate, or anhydrous sodium sulphate, or passing through a hydrophobic frit, may be employed. Conventional methods of purification, for example crystallisation and chromatography, for example silica chromatography or reverse-phase chromatography, may be used as required. Crystallisation may be performed using conventional solvents such as ethyl acetate or methanol, ethanol, or butanol, and aqueous mixtures thereof. It will be appreciated that specific reaction times temperatures may typically be determined by reaction-monitoring techniques, for example thin-layer chromatography and LC-MS.

Where appropriate individual isomeric forms of the compounds of the invention may be prepared as individual isomers using conventional procedures such as the fractional crystallisation of diastereoisomeric derivatives or chiral high performance liquid chromatography (chiral HPLC).

The absolute stereochemistry of compounds may be determined using conventional methods, such as X-ray crystallography.

Methods of Use

Examples of disease states in which the compounds of formula (I) and pharmaceutically acceptable salts thereof have potentially beneficial effects include allergic diseases and other inflammatory conditions for example allergic rhinitis and asthma, infectious diseases, and cancer. The compounds of formula (I) and pharmaceutically acceptable salts thereof are also of potential use as vaccine adjuvants.

As modulators of the immune response the compounds of formula (I) and pharmaceutically acceptable salts thereof may also be useful in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

It will be appreciated by those skilled in the art that references herein to treatment or therapy may, depending on the condition, extend to prophylaxis as well as the treatment of established conditions. There is thus provided as a further aspect of the invention a compound of formula (I), or a pharmaceutically acceptable salt thereof, for use in therapy.

It will be appreciated that, when a compound of formula (I) or a pharmaceutically acceptable salt thereof is used in therapy, it is used as an active therapeutic agent.

There is also therefore provided a compound of formula (I), or a pharmaceutically acceptable salt thereof, for use in the treatment of allergic diseases and other inflammatory conditions, infectious diseases or cancer.

There is also therefore provided a compound of formula (I), or a pharmaceutically acceptable salt thereof, for use in the treatment of allergic rhinitis.

There is also therefore provided a compound of formula (I), or a pharmaceutically acceptable salt thereof, for use in the treatment of asthma.

There is further provided the use of a compound of formula (I), or a pharmaceutically acceptable salt thereof, in the manufacture of a medicament for the treatment of allergic diseases and other inflammatory conditions, infectious diseases or cancer.

There is further provided the use of a compound of formula (I), or a pharmaceutically acceptable salt thereof, in the manufacture of a medicament for the treatment of allergic rhinitis.

There is further provided the use of a compound of formula (I), or a pharmaceutically acceptable salt thereof, in the manufacture of a medicament for the treatment of asthma.

There is further provided a method of treatment of allergic diseases and other inflammatory conditions, infectious diseases or cancer, which method comprises administering to a human subject in need thereof, a therapeutically effective amount of a compound of formula (I), or a pharmaceutically acceptable salt thereof.

There is further provided a method of treatment of allergic rhinitis, which method comprises administering to a human subject in need thereof, a therapeutically effective amount of a compound of formula (I), or a pharmaceutically acceptable salt thereof.

There is further provided a method of treatment of asthma, which method comprises administering to a human subject in need thereof, a therapeutically effective amount of a compound of formula (I), or a pharmaceutically acceptable salt thereof.

The compounds of formula (I) and pharmaceutically acceptable salts thereof are also of potential use as vaccine adjuvants.

There is thus provided as a further aspect of the invention a vaccine composition comprising a compound of formula (I), or a pharmaceutically acceptable salt thereof, and an antigen or antigen composition for use in therapy.

There is thus provided as a further aspect of the invention the use of a compound of formula (I), or a pharmaceutically acceptable salt thereof, and an antigen or antigen composition in the manufacture of a medicament for use in therapy.

There is further provided a method of treating or preventing disease comprising the administration to a human subject suffering from or susceptible to disease, a vaccine composition comprising a compound of formula (I), or a pharmaceutically acceptable salt thereof, and an antigen or antigen composition.

There is further provided the use of a vaccine composition for the manufacture of a medicament for therapy.

Compositions

The compounds of formula (I) and pharmaceutically acceptable salts thereof will normally, but not necessarily, be formulated into pharmaceutical compositions prior to administration to a patient. Accordingly, in another aspect of the invention there is provided a pharmaceutical composition comprising a compound of formula (I), or a pharmaceutically acceptable salt thereof, and one or more pharmaceutically acceptable excipients.

The compounds of formula (I) and pharmaceutically acceptable salts thereof may be formulated for administration in any convenient way. The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan monooleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or (a) pharmaceutically acceptable salt(s) thereof to be delivered to all areas of the nasal cavities (the target tissue) and further, may permit the compound(s) of formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing.

Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. The compound of formula (I), or a pharmaceutically acceptable salt thereof, may be formulated as a suspension or solution. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. Alternatively, the fluid dispenser for delivery of a fluid composition to the nasal cavities may be designed to be dose-limited, for example a single use dispenser comprising a single dose. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as antioxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of formula (I), or a pharmaceutically acceptable salt thereof.

There is further provided a vaccine composition comprising a compound of formula (I), or a pharmaceutically acceptable salt thereof, and an antigen or antigen composition.

The compounds of formula (I) and pharmaceutically acceptable salts thereof may be employed alone or in combination with other therapeutically-active agents. The invention provides in a further aspect, a combination comprising a compound of formula (I), or a pharmaceutically acceptable salt thereof, together with at least one other therapeutically-active agent.

The compounds of formula (I) and pharmaceutically acceptable salts thereof and the other therapeutically-active agent(s) may be administered together or separately and, when administered separately, administration may occur simultaneously or sequentially, in any order. The amounts of the compound(s) of formula (I) or (a) pharmaceutically acceptable salt(s) thereof and the other therapeutically-active agent(s) and the relative timings of administration will be selected in order to achieve the desired combined therapeutic effect. The administration of a combination of a compound of formula (I) or a pharmaceutically acceptable salt thereof with other treatment agents may be by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

The compounds of formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans suffering from frailty, generally, should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 0.1 micrograms to 1 mg per day, for example 1 µg, 10 µg or 100 µg. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the patient, and the particular route of administration chosen. In one aspect of the invention, a compound of formula (I), or a pharmaceutically acceptable salt thereof, may be administered once weekly for a period of 4 to 8 weeks, for example 4, 5, 6, 7 or 8 weeks. Repeat treatment cycles may be required.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There is also provided a process for preparing such a pharmaceutical composition which comprises admixing a compound of formula (I), or a pharmaceutically acceptable salt thereof, with one or more pharmaceutically acceptable excipients.

Abbreviations

The following list provides definitions of certain abbreviations as used herein. It will be appreciated that the list is not exhaustive, but the meaning of those abbreviations not herein below defined will be readily apparent to those skilled in the art.
DCM Dichloromethane
DMF N, N-Dimethylformamide
DMSO Dimethylsulphoxide
DME 1, 2-Dimethoxyethane
THF Tetrahydrofuran
EtOAc Ethyl acetate
MeOH Methanol
EtOH Ethanol
MeCN Acetonitrile
HCl Hydrochloric acid
HPLC High performance liquid chromatography
IPA iso-Propanol
MDAP Mass Directed Autopreparative HPLC
SPE Solid phase extraction
MeOH Methanol
TFA Trifluoroacetic acid
DIPEA N, N-Diisopropylethylamine

EXPERIMENTAL DETAILS

NMR $^1$H NMR spectra were recorded in either CDCl$_3$ or DMSO-d$_6$ on either a Bruker DPX 400 or Bruker Avance DRX, Varian Unity 400 spectrometer or JEOL Delta all working at 400 MHz. The internal standard used was either tetramethylsilane or the residual protonated solvent at 7.25 ppm for CDCl$_3$ or 2.50 ppm for DMSO-d$_6$.

LCMS

System A

Column: 50 mm×2.1 mm ID, 1.7 μm Acquity UPLC BEH C$_{18}$

Flow Rate: 1 mL/min.

Temp: 40° C.

UV detection range: 210 to 350 nm

Mass spectrum: Recorded on a mass spectrometer using alternative-scan positive and negative mode electrospray ionisation Solvents: A: 0.1% v/v formic acid in water
B: 0.1% v/v formic acid acetonitrile Gradient:

| Time (min.) | A % | B % |
|---|---|---|
| 0 | 97 | 3 |
| 1.5 | 0 | 100 |
| 1.9 | 0 | 100 |
| 2.0 | 97 | 3 |

System B

Column: 50 mm×2.1 mm ID, 1.7 μm Acquity UPLC BEH C$_{18}$

Flow Rate: 1 mL/min.

Temp: 40° C.

UV detection range: 210 to 350 nm

Mass spectrum: Recorded on a mass spectrometer using alternative-scan positive and negative mode electrospray ionisation Solvents: A: 10 mM ammonium bicarbonate in water adjusted to pH10 with ammonia solution
B: acetonitrile Gradient:

| Time (min.) | A % | B % |
|---|---|---|
| 0 | 99 | 1 |
| 1.5 | 3 | 97 |
| 1.9 | 3 | 97 |
| 2.0 | 0 | 100 |

Mass Directed Autopreparative HPLC (MDAP)

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A

Method A was conducted on a Sunfire C$_{18}$ column (typically 150 mm×30 mm i.d. 5 μm packing diameter) at ambient temperature. The solvents employed were:

A=0.1% v/v solution of formic acid in water

B=0.1% v/v solution of formic acid in acetonitrile.

Method B

Method B was conducted on an XBridge C$_{18}$ column (typically 100 mm×30 mm i.d. 5 μm packing diameter) at ambient temperature. The solvents employed were:

A=10 mM aqueous ammonium bicarbonate adjusted to pH 10 with ammonia solution.

B=acetonitrile.

INTERMEDIATE PREPARATION

Intermediate 1: 5-Butyl-3-iodo-1H-pyrazolo[4,3-d] pyrimidin-7(6H)-one

A 4M solution of hydrogen chloride in 1,4-dioxane (19.4 mL, 78 mmol) was added to a suspension of ethyl 4-amino-1H-pyrazole-5-carboxylate hydrochloride (2 g, 10.44 mmol) in valeronitrile (94 mL) at room temperature. The resultant mixture was stirred at 80° C. for 22 hours. The cooled reaction mixture was evaporated in-vacuo to yield a brown solid which was dissolved in ethanol (29 mL), added to a solution of sodium hydroxide (1.67 g, 41.7 mmol) in water (7.1 mL) and stirred at 100° C. for 1 hour. The reaction was cooled to room temperature, diluted with water (65 mL) and the pH adjusted to 10 using 2M aqueous citric acid solution. The reaction mixture was extracted with ethyl acetate (220 mL). The organic phase was separated, passed through a hydrophobic frit and evaporated in-vacuo to yield a brown solid. The retained aqueous was adjusted to pH 7 using 2M aqueous citric acid solution and extracted with ethyl acetate (220 mL). The organic phase was separated, passed through a hydrophobic frit and evaporated in-vacuo to yield a brown solid. The two batches of brown solid were combined to yield a solid (3.3 g). N-Iodosuccinimide (3.52 g, 15.66 mmol) was added portionwise to a solution of the solid (3.3 g) in anhydrous N,N-dimethylformamide (43 mL) at room temperature. The mixture was stirred at 60° C. for 2 hours. The cooled reaction was evaporated in-vacuo and partitioned between ethyl acetate and water/brine (1:1). The organic layer was separated, passed through a hydrophobic frit and evaporated in-vacuo to yield a brown solid (6.3 g). The solid was dissolved in ethyl acetate, loaded onto 2×50 g ISOLUTE NH$_2$ cartridges and purified using ethyl acetate (2×400 mL), 5% methanol in dichloromethane (2×200 mL), 10% methanol in dichloromethane (2×100 mL), 15% methanol in dichloromethane (2×100 mL) and finally 20% methanol in dichloromethane (2×700 mL) as eluent. Appropriate fractions were combined and evaporated in-vacuo to yield the title compound as a white solid (2.12 g).

LCMS (System A): $t_{RET}$=0.79 min; MH$^+$ 319

Intermediate 2: 1-(Hex-5-yn-1-yl)piperidine

A solution of 6-chlorohex-1-yne (5 mL, 41.3 mmol), piperidine (4.08 mL, 41.3 mmol) and sodium hydrogen carbonate (4.16 g, 49.5 mmol) in DMF (50 mL) was refluxed for 16 hours. The reaction was concentrated in-vacuo and the residue partitioned between ether (150 mL) and water (150 mL). The organic was separated and the aqueous back extracted with diethyl ether (50 mL). The combined organics were washed with brine (150 mL), dried (MgSO$_4$), filtered and concentrated in vacuo to give a crude sample of the title compound (3.74 g). Oxalic acid (2.161 g, 24 mmol) was added to the crude product. The resultant solid was recrystallised from ethanol, collected by filtration and dried in-vacuo to give 1-(hex-5-yn-1-yl)piperidine oxalic acid salt (4.66 g). The solid was partitioned between diethyl ether (150 mL) and saturated aqueous sodium bicarbonate (150 mL). The organic was separated and dried (MgSO$_4$) filtered and concentrated in vacuo to give the title compound as a yellow oil (1.93 g).

$^1$H NMR (400 MHz, CHLOROFORM-d) δppm 2.31-2.52 (m, 6H) 2.18-2.26 (m, 2H) 1.92-1.96 (m, 1H) 1.40-1.72 (m, 10H)

Intermediate 3: 5-Butyl-3-(6-(piperidin-1-yl)hexyl)-1H-pyrazolo[4,3-d]pyrimidin-7(6H)-one To a degassed solution of 5-butyl-3-iodo-1H-pyrazolo[4,3-d]pyrimidin-7(6H)-one (300 mg, 0.943 mmol) in anhydrous N,N-dimethylformamide (7 mL) under nitrogen atmosphere at room temperature was added copper(I) iodide (36 mg, 0.189 mmol), tetrakis(triphenylphosphine)-palladium (0) (120 mg, 0.104 mmol) and finally triethylamine (0.289 mL, 2.075 mmol). The mixture was stirred at room temperature under nitrogen atmosphere for 10 minutes and then a solution of 1-(5-hexyn-1-yl)piperidine (343 mg, 2.075 mmol) in anhydrous N,N-dimethylformamide (1 mL) was added. The reaction mixture was stirred at room temperature for 23 hours. The reaction was evaporated in-vacuo to yield a brown oil, the oil was diluted with dichloromethane (15 mL), loaded onto a 70 g ISOLUTE NH$_2$ cartridge and purified by chromatography using a 0-25% methanol in dichloromethane gradient over 80 minutes (UV collection wavelength set to 233 nm). Appropriate fractions were combined and evaporated in-vacuo to yield a pale yellow oil (330 mg). A solution of the oil (330 mg) in ethanol (50 mL) was passed through the H-cube (settings: 45° C., full hydrogen, 1 mL/min flow rate and 10% palladium on carbon CatCart30 as the catalyst). The solution was evaporated in-vacuo to yield a colourless oil. The oil was dissolved in MeOH:DMSO (1:1) (4×1 mL) and purified by MDAP (Method B). Appropriate fractions were combined and evaporated in-vacuo to yield a white solid (205 mg) A solution of the solid (205 mg) in ethanol (40 mL) was passed through the H-cube (settings: 45° C., full hydrogen, 1 mL/min flow rate and 10% palladium on carbon CatCart30 as the catalyst). The solution was evaporated in-vacuo to yield the title compound a white solid (201 mg).

LCMS (System B): t$_{RET}$=0.93 min; MH$^+$ 360

Intermediate 4: 3-Iodo-5-(2-methoxyethyl)-1H-pyrazolo[4,3-d]pyrimidin-7(6H)-one

A 4M solution of hydrogen chloride in 1,4-dioxane (5.19 mL, 20.74 mmol) was added to a suspension of ethyl 4-amino-1H-pyrazole-5-carboxylate hydrochloride (535 mg, 2.79 mmol) in 3-methoxypropanenitrile (25.7 mL, 240 mmol) at room temperature. The resultant mixture was stirred at 80° C. for 2.5 hours. The cooled reaction mixture was evaporated in-vacuo to yield a pale yellow solid which was dissolved in ethanol (7.7 mL), added to a solution of sodium hydroxide (447 mg, 11.17 mmol) in water (1.9 mL) and stirred at room temperature for 20 minutes. The reaction was evaporated in-vacuo to yield a brown solid. N-Iodosuccinimide (942 mg, 4.19 mmol) was added portionwise to a solution of the above compound in anhydrous N,N-dimethylformamide (DMF) (11.3 mL) at room temperature. The mixture was stirred at 60° C. for 45 minutes. The cooled reaction was evaporated in-vacuo. The residue was dissolved in the minimum volume of dichloromethane, loaded onto a 2×50 g ISOLUTE NH$_2$ cartridge and purified by chromatography using a 0-50% MeOH/DCM gradient over 60 minutes. Appropriate fractions were combined and evaporated in-vacuo to yield a cream solid (203 mg). Impure fractions from the column containing desired product were combined, concentrated in vacuo then repurified by chromatography using the same method as above. The products from both columns were combined to give the title compound as a yellow solid (309 mg).

LCMS (System A): t$_{RET}$=0.54 min; MH$^+$ 321

Intermediate 5: 5-(2-Methoxyethyl)-3-(6-(piperidin-1-yl)hexyl)-1H-pyrazolo[4,3-d]pyrimidin-7(6H)-one To a degassed solution of 3-iodo-5-(2-methoxyethyl)-1H-pyrazolo[4,3-d]pyrimidin-7(6H)-one (232 mg, 0.724 mmol) in anhydrous N,N-dimethylformamide (5 mL) under a nitrogen atmosphere at room temperature was added copper(I) iodide (27.6 mg, 0.145 mmol), tetrakis(triphenylphosphine)-palladium(0) (92 mg, 0.080 mmol) and finally triethylamine (0.222 mL, 1.592 mmol). The mixture was stirred at room temperature under nitrogen atmosphere for 10 minutes and then a solution of 1-(5-hexyn-1-yl)piperidine (263 mg, 1.592 mmol) in anhydrous N,N-dimethylformamide (1 mL) was added. The reaction mixture was stirred at room temperature for 20 hours then heated to 55° C. and left to stir for 5 hours. The reaction was evaporated in-vacuo to yield a brown oil. The oil was diluted with dichloromethane, loaded onto a 50 g ISOLUTE NH$_2$ cartridge and purified by chromatography using a 0-50% methanol in dichloromethane gradient over 60 minutes (UV collection wavelength set to 230 nm). Appropriate fractions were combined and evaporated in-vacuo to yield a pale yellow oil (188 mg). A solution of the oil (188 mg) in ethanol (30 mL) was passed through the H-cube (settings: 45° C., full hydrogen, 1 mL/min flow rate and 10% palladium on carbon CatCart30 as the catalyst). The solution was evaporated in-vacuo to yield a pale yellow oil and the crude product was purified by MDAP (Method B). Appropriate fractions were combined and evaporated in-vacuo to yield the title compound as a clear oil (117 mg).

LCMS (System B): t$_{RET}$=0.76 min; MH$^+$ 362

Intermediate 6: 5-Butyl-3-(6-chlorohex-1-yn-1-yl)-1H-pyrazolo[4,3-d]pyrimidin-7(6H)-one To a solution of 5-butyl-3-iodo-1H-pyrazolo[4,3-d]pyrimidin-7(6H)-one (4.97 g, 15.62 mmol) in N,N-dimethylformamide (100 mL) was added bis(triphenylphosphine)palladium(II)dichloride (1.228 g, 1.750 mmol) and copper(I) iodide (0.595 g, 3.12 mmol). The solution was stirred and degassed with nitrogen for 5 minutes then the reaction mixture placed under a nitrogen atmosphere. A solution of 6-chloro-1-hexyne (3.64 g, 31.2 mmol) and triethylamine (4.36 mL, 31.2 mmol) in N,N-dimethylformamide (30 mL) was added dropwise over 10 minutes. The reaction mixture was stirred at ambient temperature for a further 10 minutes then heated to 60° C. for 2.5 hours. The reaction mixture was concentrated in vacuo at 60° C. and the resulting residue partitioned between ethyl acetate (250 mL) and a 1:1 mixture of water:brine (500 mL). The organic layer was separated and the aqueous layer back extracted with ethyl acetate (250 mL). The combined organic phases were dried through a hydrophobic frit and concentrated in vacuo to give a brown solid (8.0 g). The residue was dissolved in a 1:1 mixture of MeOH:DCM and absorbed onto Florisil. The solid was loaded and purified by chromatography on silica (330 g) using a 0-100% ethyl acetate-cyclohexane gradient over 10 column volumes followed by flushing with ethyl acetate for 9 column volumes. The appropriate fractions were combined and evaporated in vacuo to give a yellow solid (3.55 g). The solid was triturated with diisopropyl ether, filtered and dried in vacuo at 50° C. to give the title compound as a pale yellow solid (3.14 g).

LCMS (System B): $t_{RET}$=0.98 min; MH$^+$ 307, 309

Intermediate 7: 5-Butyl-3-(6-(pyrrolidin-1-yl)hexyl)-1H-pyrazolo[4,3-d]pyrimidin-7(6H)-one To a suspension of 5-butyl-3-(6-chlorohex-1-yn-1-yl)-1H-pyrazolo[4,3-d]pyrimidin-7(6H)-one (2.59 g, 8.44 mmol) in anhydrous acetonitrile (115 mL) was added pyrrolidine (2.11 mL, 25.3 mmol) and triethylamine (3.53 mL, 25.3 mmol). The reaction was stirred at 80° C. for 3.5 hours. A further 2.11 mL (25.3 mmol) of pyrrolidine and 3.53 mL (25.3 mmol) of triethylamine were added to the reaction. The reaction was stirred at 80° C. for a further 18 hours. The cooled reaction was partitioned between ethyl acetate and water. The organic layer was separated, passed through a hydrophobic frit and evaporated in-vacuo to yield a yellow oil (1.9 g). The retained aqueous was re-extracted with 20% methanol in dichloromethane. The organic layer was passed through a hydrophobic frit and evaporated in-vacuo to yield a yellow oil (1.02 g). The two yellow oils were combined to yield a yellow oil (2.92 g). A mixture of the oil and 10 wt % palladium on carbon (350 mg) in ethanol (120 mL) was stirred under a hydrogen atmosphere at room temperature for 90 minutes. A further 350 mg of 10 wt % palladium on carbon was added to the reaction under a nitrogen atmosphere and the reaction was stirred under a hydrogen atmosphere at room temperature for 60 minutes. A further 350 mg of 10 wt % palladium on carbon was added to the reaction under a nitrogen atmosphere and the reaction was stirred under a hydrogen atmosphere at room temperature for 60 minutes. The reaction mixture was filtered through a 10 g celite cartridge and the filtrate evaporated in-vacuo to yield a yellow oil (2.8 g). The oil was dissolved in the minimum volume of dichloromethane, loaded onto a 375 g Biotage KP-NH cartridge and purified using a 0-10% methanol in dichloromethane gradient over 12 column volumes followed by 10% methanol in dichloromethane over 3 column volumes. Appropriate fractions were combined and evaporated in-vacuo to yield the title compound as a pale yellow solid (1.845 g).

LCMS (System B): $t_{RET}$=0.85 min; MH$^+$ 346

Impure fractions from the chromatography were combined and evaporated in-vacuo to yield a yellow oil (380 mg). The oil was dissolved in MeOH:DMSO (1:1) (4×1 ml) and purified by MDAP (Method B). Appropriate fractions were combined and evaporated in-vacuo to yield a further portion of the title compound a pale yellow oil (198 mg).

Intermediate 8: 5-Butyl-N-(3,4-dimethoxybenzyl)-3-iodo-1H-pyrazolo[4,3-d]pyrimidin-7-amine To a solution of 5-butyl-3-iodo-1H-pyrazolo[4,3-d]pyrimidin-7(6H)-one (5 g, 15.72 mmol) and (benzotriazol-1-yloxy)tris(dimethylamino)phosphonium hexafluorophosphate (10.43 g, 23.58 mmol) in anhydrous DMF (250 mL) at room temperature under a nitrogen atmosphere was added 1,8-diazabicyclo[5.4.0]undec-7-ene (4.23 mL, 28.3 mmol) and the reaction mixture was stirred for 2.5 hours. (3,4-Dimethoxyphenyl)methanamine (20 mL, 94 mmol) was added and the mixture was warmed to 40° C. for 3 hours. The reaction mixture was evaporated in-vacuo and the resulting oil partitioned between ethyl acetate and water. The organic layer was separated, washed with brine, dried over MgSO$_4$, filtered and evaporated in-vacuo to yield as a semi-crystalline yellow oil (23.7 g). The residue was absorbed onto Florosil, loaded onto a 330 g silica pre-conditioned cartridge and purified by chromatography using cyclohexane over 1 column volume followed by 0-100% ethyl acetate in cyclohexane gradient over 14 column volumes followed by ethyl acetate over 4 column volumes. Appropriate fractions containing only the desired material by LC-MS analysis were combined and evaporated in-vacuo to yield the title compound as a pale yellow foam (4.58 g).

LCMS (System B): $t_{RET}$=1.08-1.09 min; MH$^+$ 468

$^1$H NMR (400 MHz, DMSO-d$_6$) includes δ=7.90-7.65 (m, 1H), 7.05 (s, 1H), 6.93 (s, 2H), 4.70-4.61 (m, 2H), 3.73 (s, 6H), 2.75-2.67 (m, 2H), 1.78-1.67 (m, 2H), 1.40-1.28 (m, 2H), 0.90 (t, 3H)

Intermediate 9: 5-Butyl-3-(6-chlorohex-1-yn-1-yl)-N-(3,4-dimethoxybenzyl)-1H-pyrazolo[4,3-d]pyrimidin-7-amine A nitrogen degassed stirred mixture of 5-butyl-N-(3,4-dimethoxybenzyl)-3-iodo-1H-pyrazolo[4,3-d]pyrimidin-7-amine (4.58 g, 9.7 mmol), copper(I) iodide (278 mg, 1.46 mmol) and bis(triphenylphosphine)palladium(II)dichloride (515 mg, 0.734 mmol) in anhydrous N,N-dimethylformamide (105 mL) was warmed to 60° C. under a nitrogen atmosphere before addition of a solution of 6-chloro-1-hexyne (1.712 g, 14.69 mmol) and triethylamine (2.047 mL, 14.69 mmol) in anhydrous nitrogen degassed N,N-dimethylformamide (15 mL), dropwise over 5 minutes. The reaction was stirred at 60° C. for 6 hours. The cooled reaction mixture was evaporated in-vacuo and the resultant oil partitioned between 1:1 water/brine and ethyl acetate. The organic layer was separated, passed through a hydrophobic frit and evaporated in-vacuo to yield an orange oil. The oil was dissolved in the minimum volume of dichloromethane, loaded onto a 330 g silica pre-conditioned cartridge and purified by chromatography using cyclohexane over 1 column volume followed by 0-100% ethyl acetate in cyclohexane gradient over 14 column volumes followed by ethyl acetate over 2 column volumes. Appropriate fractions were combined and evaporated in-vacuo to yield the title compound as a yellow foam (3.334 g)

LCMS (System B): $t_{RET}$=1.26, 1.28 min; MH$^+$ 456

$^1$H NMR (400 MHz, CHLOROFORM-d) δ=6.90 (br. s., 2H), 6.81-6.70 (m, 1H), 4.77 (br. s., 2H), 3.94-3.72 (m, 6H), 3.49 (t, J=6.5 Hz, 2H), 2.88 (t, J=7.8 Hz, 2H), 2.25 (br. s., 2H), 1.90-1.71 (m, 4H), 1.62-1.52 (m, 2H), 1.48-1.31 (m, 2H), 0.93 (t, J=7.3 Hz, 3H)

Intermediate 10: 5-Butyl-N-(3,4-dimethoxybenzyl)-3-(6-(pyrrolidin-1-yl)hex-1-yn-1-yl)-1H-pyrazolo[4,3-d]pyrimidin-7-amine To a solution of 5-butyl-3-(6-chlorohex-1-yn-1-yl)-N-(3,4-dimethoxybenzyl)-1H-pyrazolo[4,3-d]pyrimidin-7-amine (3.334 g, 7.31 mmol) in anhydrous acetonitrile (4 mL) was added triethylamine (3.06 mL, 21.94 mmol) and pyrrolidine (1.831 mL, 21.94 mmol). The solution was stirred at 70° C. for 18 hours. A further equivalent of pyrrolidine (0.61 mL, 7.31 mmol) and triethylamine (1.019 mL, 7.31 mmol) were added to the reaction mixture. The solution was stirred at 70° C. for a further 3 hours. The cooled reaction mixture was evaporated in-vacuo and the residue partitioned between ethyl acetate and water/brine (1:1). The organic phase was separated, passed through a hydrophobic frit and evaporated in-vacuo to yield a sticky brown gum (4.226 g). The gum was dissolved in the minimum volume of dichloromethane, loaded onto a 340 g silica pre-conditioned cartridge and purified by chromatography using dichloromethane over 1 column volume followed by 0-30% methanol (+1% triethylamine) in dichloromethane gradient over 14 column volumes followed by 30% methanol (+1% triethylamine) in dichloromethane over 3 column volumes. Appropriate fractions were combined and evaporated in-vacuo to yield the title compound as a sticky brown gum (1.838 g).

LCMS (System B): $t_{RET}$=1.11-1.17 min; MH$^+$ 491

$^1$H NMR (400 MHz, METHANOL-d$_4$) includes δ=7.07-7.04 (m, 1H), 7.00-6.95 (m, 1H), 6.92 (s, 1H), 4.76 (s, 2H), 3.83-3.78 (m, 6H), 2.82-2.56 (m, 10H), 1.90-1.67 (m, 10H), 1.44-1.32 (m, 2H), 0.94 (t, J=7.3 Hz, 3H)

Intermediate 11: 3-(6-Chlorohex-1-yn-1-yl)-5-(2-methoxyethyl)-1H-pyrazolo[4,3-d]pyrimidin-7(6H)-one To a nitrogen degassed solution of 3-iodo-5-(2-methoxyethyl)-1H-pyrazolo[4,3-d]pyrimidin-7(6H)-one (307 mg, 0.959 mmol) in anhydrous N,N-dimethylformamide (6 mL) under a nitrogen atmosphere at room temperature was added copper(I) iodide (36.5 mg, 0.192 mmol), bis(triphenylphosphine)palladium(II)dichloride (75 mg, 0.107 mmol) and finally triethylamine (0.267 mL, 1.918 mmol). The mixture was stirred at room temperature under nitrogen atmosphere for 10 minutes and then a solution of 6-chlorohex-1-yne (224 mg, 1.918 mmol) in anhydrous N,N-dimethylformamide (1.5 mL) was added. The reaction mixture was stirred at 60° C. for 2 hours. Another 2 equivalents of 6-chlorohex-1-yne (224 mg, 1.918 mmol) and the reaction was left to stir at 60° C. for 1 hour. The reaction was evaporated in-vacuo to yield a dark red oil. The oil was partitioned between water/brine (1:1) and ethyl acetate. The organic layer was separated, passed through a hydrophobic frit and evaporated in-vacuo to yield an orange oil (621 mg). The crude material was dissolved in a minimum amount of DCM, loaded onto a 50 g silica cartridge and purified by chromatography using a 0-100% ethyl acetate in cyclohexane gradient over 60 minutes. Appropriate fractions containing desired product were combined and evaporated in-vacuo to yield the title compound as a pale yellow solid (163.5 mg).

LCMS (System A): $t_{RET}$=0.80 min; MH$^+$ 309, 311

Intermediate 12: 5-(2-Methoxyethyl)-3-(6-(pyrrolidin-1-yl)hexyl)-1H-pyrazolo[4,3-d]pyrimidin-7(6H)-one To a solution of 3-(6-chlorohex-1-yn-1-yl)-5-(2-methoxyethyl)-1H-pyrazolo[4,3-d]pyrimidin-7(6H)-one (84 mg, 0.230 mmol) in anhydrous N,N-dimethylformamide (4 mL) was added pyrrolidine (0.132 mL, 1.579 mmol) and triethylamine (0.293 mL, 2.105 mmol). The reaction was stirred at 80° C. for 2 hours. A further 66 µL (1.5 eq) of pyrrolidine and 147 µL (2 eq) of triethylamine were added to the reaction and the reaction was stirred at 80° C. for 2 hours. A further 66 µL (1.5 eq) of pyrrolidine and 147 µL (2 eq) of triethylamine were added to the reaction. The reaction was stirred at 80° C. for 1 hours. The reaction was evaporated in-vacuo to yield a dark yellow oil. A solution of the oil in ethanol (35 mL) was passed through the H-cube (settings: 55° C., full hydrogen, 1 mL/min flow rate and 10% palladium on carbon CatCart30 as the catalyst). A new 10% palladium on carbon CatCart30 cartridge was inserted into the H-cube and the solution was passed through the H-cube again (settings: 55° C., full hydrogen, 1 mL/min flow rate). The solution was evaporated in-vacuo to yield a pale yellow oil and the crude product was purified by MDAP (Method B). Appropriate fractions were combined and evaporated in-vacuo to give the title compound as a clear oil (84 mg).

LCMS (System A): $t_{RET}$=0.46 min; MH$^+$ 348

Intermediate 13: 5-Butyl-3-(5-chloropent-1-yn-1-yl)-1H-pyrazolo[4,3-d]pyrimidin-7(6H)-one To a nitrogen degassed solution of 5-butyl-3-iodo-1H-pyrazolo[4,3-d]pyrimidin-7(6H)-one (250 mg, 0.786 mmol) in anhydrous N,N-dimethylformamide (6 mL) under nitrogen atmosphere at room temperature was added copper(I) iodide (30 mg, 0.158 mmol), bis(triphenylphosphine)palladium(II)dichloride (62 mg, 0.088 mmol) and finally triethylamine (0.219 mL, 1.572 mmol). The mixture was stirred at room temperature under nitrogen atmosphere for 10 minutes and then a solution of 5-chloro-1-pentyne (161 mg, 1.572 mmol) in anhydrous N,N-dimethylformamide (1.5 mL) was added. The reaction mixture was stirred at 60° C. for 80 minutes. The reaction was evaporated in-vacuo to yield a brown oil. The oil was partitioned between water/brine (1:1) and ethyl acetate. The organic layer was separated, passed through a hydrophobic frit and evaporated in-vacuo to yield a brown solid. The solid was absorbed onto Florisil, loaded onto a 50 g silica cartridge and purified by chromatography using a 0-100% ethyl acetate in cyclohexane gradient over 60 minutes. Appropriate fractions were combined and evaporated in-vacuo to yield the title compound as a pale yellow solid (172 mg).

LCMS (System A): $t_{RET}$=0.91 min; MH$^+$ 293, 295

Intermediate 14: 5-Butyl-3-(5-(piperidin-1-yl)pentyl)-1H-pyrazolo[4,3-d]pyrimidin-7(6H)-one To a solution of 5-butyl-3-(5-chloropent-1-yn-1-yl)-1H-pyrazolo[4,3-d]pyrimidin-7(6H)-one (168 mg, 0.574 mmol) in anhydrous N,N-dimethylformamide (3.5 mL) was added a solution of piperidine (147 mg, 1.722 mmol) in anhydrous N,N-dimethylformamide (0.5 mL) and triethylamine (0.32 mL, 2.295 mmol). The reaction was stirred at 80° C. for 190 minutes. A further 73 mg (0.857 mmol) of piperidine and 160 µL (1.148 mmol) of triethylamine was added to the reaction. The reaction was stirred at 80° C. for a further 2.5 hours and then at room temperature for 15.5 hours. A further 73 mg (0.857 mmol) of piperidine and 160 µL (1.148 mmol) of triethylamine was added to the reaction. The reaction was stirred at 80° C. for 2.5 hours. The reaction was evaporated in-vacuo to yield a dark yellow oil. A solution of the oil in ethanol (50 mL) was passed through the H-cube (settings: 30° C., full hydrogen, 1 mL/min flow rate and 10% palladium on carbon CatCart30 as the catalyst). A new 10% palladium on carbon CatCart30 cartridge was inserted into the H-cube and the solution was passed through the H-cube again (settings: 30° C., full hydrogen, 1 mL/min flow rate). The solution was evaporated in-vacuo to yield a pale yellow oil. The oil was dissolved in MeOH:DMSO (1:1) (3×1 mL) and purified by MDAP (Method B). Appropriate fractions were combined and evaporated in-vacuo to yield the title compound as a pale yellow solid (91 mg).

LCMS (System B): $t_{RET}$=0.83 min; MH$^+$ 346

Intermediate 15: 5-Butyl-3-(5-(pyrrolidin-1-yl)pentyl)-1H-pyrazolo[4,3-d]pyrimidin-7(6H)-one To a degassed solution of 5-butyl-3-iodo-1H-pyrazolo[4,3-d]pyrimidin-7(6H)-one (79 mg, 0.248 mmol) in anhydrous N,N-dimethylformamide (2.0 mL) under nitrogen atmosphere at room temperature was added copper(I) iodide (10 mg, 0.053 mmol), tetrakis(triphenylphosphine)-palladium(0) (32 mg, 0.028 mmol) and finally triethylamine (0.076 mL, 0.546 mmol). The mixture was stirred at room temperature under nitrogen atmosphere for 10 minutes and then a solution of 1-(4-pentyn-1-yl)pyrrolidine (75 mg, 0.546 mmol) (Chemical Communications 46(19), 3351-3353; 2010) in anhydrous N,N-dimethylformamide (0.5 mL) was added. The reaction mixture was stirred at 55° C. for 1 hour. A solution of 1-(4-pentyn-1-yl)pyrrolidine (75 mg, 0.546 mmol) in anhydrous N,N-dimethylformamide (0.5 mL) was added to the reaction. The reaction mixture was stirred at 55° C. for 40 minutes. The reaction was evaporated in-vacuo to yield a dark yellow oil. A filtered solution of the oil in ethanol (15 mL) was passed through the H-cube (settings: 45° C., full hydrogen, 1 mL/min flow rate and 10% palladium on carbon CatCart30 as the catalyst). The solution was passed through the H-cube a further two times using a new CatCart 30 cartridge on each occasion. The solution was evaporated in-vacuo to yield a colourless oil. The oil was dissolved in MeOH:DMSO (1:1) (1 mL) and purified by MDAP (Method B). Appropriate fractions were combined and evaporated in-vacuo to yield the title compound as a white solid (20 mg).

LCMS (System B): $t_{RET}$=0.79 min; MH$^+$ 332

Intermediate 16: 5-Butyl-N-(2,4-dimethoxybenzyl)-3-iodo-1H-pyrazolo[4,3-d]pyrimidin-7-amine A solution of 5-butyl-3-iodo-1H-pyrazolo[4,3-d]pyrimidin-7(6H)-one (50 g, 157 mmol), (2,4-dimethoxyphenyl)methanamine (60 g, 359 mmol) and 2,3,4,6,7,8,9,10-octahydropyrimido[1,2-a]azepine (47.9 g, 314 mmol) in acetonitrile (500 mL) was treated with ((1H-benzo[d][1,2,3]triazol-1-yl)oxy)tri(pyrrolidin-1-yl)phosphonium hexafluorophosphate(V) (100 g, 192 mmol) and stirred for 6 hours at room temperature under nitrogen. The resulting suspension was filtered to remove precipitate and the filtrate was evaporated. The residue was purified on a silica cartridge (1500 g) (applied in minimum DCM) eluted with 0-80% cyclohexane-EtOAc (12 column volumes). Product-containing fractions were part evaporated to give a heavy suspension that was filtered and the solid air-dried to give the title compound (37.5 g, 80 mmol) as a white powder.

LCMS (System A): $t_{RET}$=0.91 min; MH$^+$ 468
$^1$H NMR (400 MHz, CHLOROFORM-d) includes δ=6.43-6.33 (m, 2H), 4.76 (s, 2H), 3.79 (s, 3H), 3.67 (s, 3H), 2.90-2.80 (m, 2H), 1.84 (s, 2H), 1.48-1.35 (m, 2H), 0.94 (t, J=7.3 Hz, 3H)

The mother liquors and impure fractions were evaporated to give yellow solids. The combined impure materials were triturated with ethyl acetate to give a cream solid (30 g). Further trituration with diethyl ether (50 mL) followed by DCM/Et$_2$O (1;1, 30 mL) gave an additional portion of the title compound as a white solid (25.7 g).

Intermediate 17: 5-Butyl-3-(6-chlorohex-1-yn-1-yl)-N-(2,4-dimethoxybenzyl)-1H-pyrazolo[4,3-d]pyrimidin-7-amine A solution of 5-butyl-N-(2,4-dimethoxybenzyl)-3-iodo-1H-pyrazolo[4,3-d]pyrimidin-7-amine (50 g, 107 mmol), 6-chloro-1-hexyne (18.71 g, 160 mmol), triethylamine (22.37 mL, 160 mmol), bis(triphenylphosphine)palladium(II)dichloride (5.63 g, 8.02 mmol) and copper(I) iodide (3.04 g, 15.94 mmol) in N,N-Dimethylformamide (1000 mL) under nitrogen was heated to 70° C. for 4 hours. The cooled solution was evaporated and the residue was purified by chromatography on a 1.5 kg silica cartridge eluted with 20-80% cyclohexane—EtOAc during 12 column volumes. Appropriate fractions were evaporated to give the title compound as a yellow foam (25.5 g).

LCMS (System A): $t_{RET}$=1.05 min; MH$^+$ 456, 458
$^1$H NMR (400 MHz, CHLOROFORM-d) includes δ=6.71-6.54 (m, 1H), 6.41-6.31 (m, 2H), 4.75 (br. s., 2H), 3.77 (s, 4H), 3.67 (br. s., 3H), 3.50-3.43 (m, 2H), 2.89-2.76 (m, 3H), 2.26-2.15 (m, 2H), 1.30-1.20 (m, 1H), 0.92 (t, J=7.3 Hz, 3H)

Intermediate 18: 5-Butyl-N-(2,4-dimethoxybenzyl)-3-(6-(pyrrolidin-1-yl)hex-1-yn-1-yl)-1H-pyrazolo[4,3-d]pyrimidin-7-amine A solution of 5-butyl-3-(6-chlorohex-1-yn-1-yl)-N-(2,4-dimethoxybenzyl)-1H-pyrazolo[4,3-d]pyrimidin-7-amine (30 g, 65.8 mmol), pyrrolidine (16.32 mL, 197 mmol) and Et$_3$N (27.5 mL, 197 mmol) in Acetonitrile (400 mL) was heated at 70° C. for 16 hours. Further pyrrolidine (7 g) was added and the solution was heated at 70° C. for 8 hours. The cooled solution was evaporated and the residue was purified on a silica cartridge (750 g) eluted with EtOAc (2 column volumes) followed by 20-30% MeOH (+1% Et$_3$N)/EtOAc (16 column volumes) to give the title compound as a yellow gum (23.3 g).

LCMS (System B): $t_{RET}$=1.15 min; MH$^+$ 491
$^1$H NMR (400 MHz, CHLOROFORM-d) includes δ=7.31-7.25 (m, 1H), 6.42-6.23 (m, 2H), 4.76 (br. S., 2H), 3.76 (s, 3H), 3.65 (s, 3H), 2.88-2.78 (m, 6H), 2.67-2.60 (m, 2H), 2.18-2.11 (m, 2H_, 1.93-1.75 (m, 6H), 1.63 (br. S., 2H), 1.43-1.28 (m, 4H), 0.91 (t, J=7.3 Hz, 3H).

Intermediate 19: 5-Butyl-N-(2,4-dimethoxybenzyl)-3-(6-(pyrrolidin-1-yl)hexyl)-1H-pyrazolo[4,3-d]pyrimidin-7-amine A solution of 5-butyl-N-(2,4-dimethoxybenzyl)-3-(6-(pyrrolidin-1-yl)hex-1-yn-1-yl)-1H-pyrazolo[4,3-d]pyrimidin-7-amine (20 g, 40.8 mmol) in ethanol (500 mL) was hydrogenated over Pd—C (5 g, 4.70 mmol) for 4 hour (H$_2$ uptake complete). The mixture was filtered through Hyflo and evaporated. The residue in DCM (30 mL) was purified on a 120 g silica cartridge (Redisep Gold) eluted with toluene-ethanol-NH$_3$ (85/15/1.5) in 7 batches—taking off product and lower running impurity and recycling the cartridge each time (total volume~3 litres). Evaporation of appropriate fractions gave the title compound as a yellow gum (16.3 g).

LCMS (System B): $t_{RET}$=1.15 min; MH$^+$ 495
$^1$H NMR (400 MHz, CHLOROFORM-d) includes δ=6.49-6.41 (m, 2H), 6.12-6.02 (m, 1H), 4.82 (br. s., 2H), 3.85-3.78 (m, 6H), 3.04-2.96 (m, 2H), 2.88-2.80 (m, 2H), 2.57 (br. s., 4H), 2.50-2.43 (m, 2H), 0.97 (t, J=7.3 Hz, 3H)

Intermediate 20: 7-(5-Butyl-7-((2,4-dimethoxybenzyl)amino)-1H-pyrazolo[4,3-d]pyrimidin-3-yl)heptan-1-ol Bis(triphenylphosphine)palladium(II)dichloride (68 mg, 0.097 mmol), triethylamine (0.537 mL, 3.85 mmol) and copper iodide (37 mg, 0.194 mmol) were added to a nitrogen degassed solution of 5-butyl-N-(2,4-dimethoxybenzyl)-3-iodo-1H-pyrazolo[4,3-d]pyrimidin-7-amine (600 mg, 1.284 mmol) in anhydrous N,N-dimethylformamide (15 mL). The mixture was stirred under a nitrogen atmosphere and heated to 60° C. before the addition of hept-6-yn-1-ol (432 mg, 3.85 mmol) in anhydrous N,N-dimethylformamide (2 mL). The reaction was stirred at 60° C. for 2.5 hours. An additional 0.5 equivalents of hept-6-yn-1-ol (72 mg, 0.642 mmol) in anhydrous N,N-dimethylformamide (0.5 mL) was added to the reaction. The mixture was stirred for a further 2.5 hours under a nitrogen atmosphere at 60° C. A further 0.5 equivalents of hept-6-yn-1-ol (72 mg, 0.642 mmol) in anhydrous N,N-dimethylformamide (0.5 mL) was added to the reaction. The mixture was stirred for a further 4 hours under a nitrogen atmosphere at 60° C. and then allowed to cool to ambient temperature overnight. The reaction mixture was evaporated in-vacuo to yield a brown oil. The resulting oil was partitioned between ethyl acetate (25 mL) and water/brine (1:1, 15 mL). The organic layer was separated and the aqueous phase back-extracted with ethyl acetate (25 mL). The combined organic extracts were passed through a hydrophobic frit and evaporated in-vacuo to yield the intermediate alkyne as an orange oil (1.21 g).

A mixture of the oil and 10% palladium on carbon (200 mg) in ethanol (20 mL) was stirred under a hydrogen atmosphere for 22 hours. The reaction was filtered through a celite cartridge (10 g) and evaporated in-vacuo to yield an orange oil. The oil was dissolved in the minimum volume of dichloromethane, loaded onto a 50 g silica cartridge and purified using a 0-100% ethyl acetate in cyclohexane gradient over 60 minutes followed by elution with ethyl acetate (300 mL) then 10% methanol in dichloromethane (70 mL). Appropriate fractions were combined and evaporated in vacuo to yield an orange oil. The oil was dissolved in the minimum volume of dichloromethane, loaded onto a 50 g silica cartridge and purified using a 0-10% methanol in dichloromethane gradient over 40 mins. (detection wavelength=230 nm). Appropriate fractions were combined and evaporated in vacuo to yield a yellow oil (380 mg). A mixture of the oil and 10% palladium on carbon (200 mg) in ethanol (20 mL) was stirred under a hydrogen atmosphere for 20 hours. The reaction was filtered through a celite cartridge (10 g) and evaporated in-vacuo to yield the title compound as a pale yellow oil (264 mg).

LCMS (System B): $t_{RET}$=1.17 min; MH$^+$ 456

Intermediate 21: 3-(7-Bromoheptyl)-5-butyl-N-(2,4-dimethoxybenzyl)-1H-pyrazolo[4,3-d]pyrimidin-7-amine A solution of triphenylphosphine (182 mg, 0.695 mmol) in dichloromethane (2 mL) was added dropwise to a stirred solution of 7-(5-butyl-7-((2,4-dimethoxybenzyl)amino)-1H-pyrazolo[4,3-d]pyrimidin-3-yl)heptan-1-ol (264 mg, 0.579 mmol) and carbon tetrabromide (231 mg, 0.695 mmol) in dichloromethane (5 mL). The reaction was stirred at room temperature for 18 hours. An additional portion of carbon tetrabromide (231 mg, 0.695 mmol) and triphenylphosphine (182 mg, 0.695 mmol) were added to the reaction mixture. Stirring at ambient temperature was continued for 2 hours. The solvent was evaporated in-vacuo to yield a yellow oil. The oil was dissolved in anhydrous dichloromethane (DCM) (7 mL) and stirred at room temperature for 1.5 hours. Carbon tetrabromide (231 mg, 0.695 mmol) and triphenylphosphine (182 mg, 0.695 mmol) were added to the reaction mixture. Stirring at ambient temperature was continued for 17.5 hours. Additional carbon tetrabromide (115 mg, 0.348 mmol) and triphenylphosphine (91 mg, 0.348 mmol) were added to the reaction mixture. Stirring at ambient temperature was continued for 2 hours. The reaction was evaporated in-vacuo to yield a clear oil. The resulting oil was partitioned between ethyl acetate (10 mL) and water/brine (1:1, 15 mL). The organic layer was separated, passed through a hydrophobic frit and evaporated in-vacuo to yield a pale yellow solid (1.40 g). The solid was dissolved in the minimum volume of dichloromethane, loaded onto a 50 g silica cartridge and purified using a 0-100% ethyl acetate in cyclohexane gradient over 60 minutes, followed by 0-20% methanol in DCM over 30 minutes. Fractions containing only one component were combined and evaporated in-vacuo to yield the title compound as a pale yellow oil (55 mg).

LCMS (System B): $t_{RET}$=1.47 min; MH$^+$ 518, 520

Fractions containing two components were combined and evaporated in-vacuo to yield an additional portion of the title compound as a 1:1 mixture with triphenyphosphine oxide as a pale yellow oil (270 mg)

LCMS (System B): $t_{RET}$=1.47 min; MH$^+$ 518, 520: 0.98 min; MH$^+$ 279

Intermediate 22: 3-(6-(Azepan-1-yl)hexyl)-5-butyl-N-(2,4-dimethoxybenzyl)-1H-pyrazolo[4,3-d]pyrimidin-7-amine To a suspension of 5-butyl-3-(6-chlorohex-1-yn-1-yl)-N-(2,4-dimethoxybenzyl)-1H-pyrazolo[4,3-d]pyrimidin-7-amine (400 mg, 0.877 mmol) and hexamethyleneimine (0.297 mL, 2.63 mmol) in acetonitrile (7 mL) was added triethylamine (0.367 mL, 2.63 mmol) at ambient temperature. The reaction mixture was stirred at 60° C. under nitrogen for 16 hours. The temperature was increased to 80° C. and the reaction mixture was left to stir under nitrogen for a further 7 hours. To the reaction mixture was added a solution of hexamethyleneimine (0.149 mL, 1.32 mmol) and triethylamine (0.184 mL, 1.32 mmol) and was left to stir under nitrogen 60° C. for a further 72 hours. The reaction mixture was evaporated in vacuo to give an brown oil which was partitioned between ethyl acetate (50 mL) and water (50 mL). The aqueous layer was extracted and the organic layer was washed with brine (50 mL), dried using a hydrophobic frit and concentrated in vacuo to give a brown oil. The oil was dissolved in minimal amount of dichloromethane, which was then loaded and purified on aminopropyl silica cartridge (50 g) using a 0-100% ethyl acetate-cyclohexane gradient followed by a 0-25% methanol-dichloromethane gradient for 60 minutes. The appropriate fractions were combined and evaporated in vacuo to give a brown oil, which was then azeotroped with dichloromethane and petroleum ether (40-60) to give a brown solid (0.185 g).

The solid was dissolved in ethanol (45 mL) and was hydrogenated using the H-cube (settings: 40° C., Full H$_2$, 1 mL/min flow rate) and 5% Pd/C CatCart 30 as the catalyst. The solvent obtained was concentrated in vacuo to give a brown oil which was dissolved in ethanol (20 mL) and was hydrogenated using the H-cube (settings: 40° C., Full H$_2$, 1 mL/min flow rate) and 5% Pd/C CatCart 30 as the catalyst. The solvent was further hydrogenated using the H-cube (settings: 40° C., Full H$_2$, 1 mL/min flow rate) and the same 5% Pd/C CatCart 30 as the catalyst. The solution obtained was evaporated in vacuo to give a brown oil. The brown oil was then dissolved in minimal amount of dichloromethane, which was then loaded and purified by chromatography on aminopropyl silica (20 g) using a 0-10% methanol-dichloromethane gradient for 40 minutes. The appropriate fractions were combined and evaporated in vacuo to give a brown oil, which was then azeotroped with dichloromethane and petroleum ether (40-60) to give the title compound as a brown oil (0.100 g).

LCMS (System B): $t_{RET}$=1.19 min; MH$^+$ 523

Intermediate 23: 5-Butyl-3-(5-chloropent-1-yn-1-yl)-N-(2,4-dimethoxybenzyl)-1H-pyrazolo[4,3-d]pyrimidin-7-amine Bis(triphenylphosphine)palladium(II)dichloride (101 mg, 0.144 mmol), triethylamine (0.403 mL, 2.89 mmol) and copper iodide (55.0 mg, 0.289 mmol) were added to a nitrogen degassed solution of 5-butyl-N-(2,4-dimethoxybenzyl)-3-iodo-1H-pyrazolo[4,3-d]pyrimidin-7-amine (900 mg, 1.926 mmol) in anhydrous N,N-dimethylformamide (23 mL). The mixture was stirred under a nitrogen atmosphere and heated to 60° C. before the addition of 5-chloropent-1-yne (296 mg, 2.89 mmol) in anhydrous N,N-dimethylformamide (2 mL). The reaction was stirred at 60° C. for 3 hours. A further 0.30 equivalents of 5-chloropent-1-yne (59 mg, 0.575 mmol) in anhydrous N,N-dimethylformamide (1 mL) was added to the reaction. The mixture was stirred at 60° C. for a further 2.5 hours and then allowed to cool to room temperature overnight. The reaction mixture was evaporated in-vacuo to yield a brown oil. The resulting oil was partitioned between ethyl acetate (25 mL) and water/brine (1:1, 10 mL). The organic layer was separated, passed through a hydrophobic frit and evaporated in-vacuo to yield a brown oil (1.32 g). The oil was dissolved in the minimum volume of dichloromethane, loaded onto a 100 g silica cartridge and purified by chromatography using a 0-100% ethyl acetate in cyclohexane gradient over 60 minutes. Appropriate fractions were combined and evaporated in-vacuo to yield an orange oil. The oil was dissolved in the minimum volume of dichloromethane, loaded onto a 100 g silica cartridge and re-purified by chromatography using a 0-100% ethyl acetate in cyclohexane gradient over 60 minutes. Appropriate fractions were combined and evaporated in-vacuo to yield the title compound as an orange oil (720 mg).

LCMS (System B): $t_{RET}$=1.32 min; MH⁺ 442, 444

Intermediate 24: (S)-5-Butyl-N-(3,4-dimethoxybenzyl)-3-(6-(3-fluoropyrrolidin-1-yl)hexyl)-1H-pyrazolo[4,3-d]pyrimidin-7-amine To a stirred solution of 5-butyl-3-(6-chlorohex-1-yn-1-yl)-N-(3,4-dimethoxybenzyl)-1H-pyrazolo[4,3-d]pyrimidin-7-amine (225 mg, 0.493 mmol) in acetonitrile (4 mL) was added triethylamine (0.413 mL, 2.96 mmol) and (S)-3-fluoropyrrolidine hydrochloride (186 mg, 1.480 mmol). The resultant mixture was heated at 60° C. for 22 hours. To the reaction mixture was added further (S)-3-fluoropyrrolidine hydrochloride (186 mg, 1.480 mmol) and further triethylamine (0.413 mL, 2.96 mmol) and heating at 75° C. continued for 20 hours. The reaction mixture was concentrated in vacuo and the residue partitioned between DCM (20 mL) and water (20 mL). The organic was separated and dried using a hydrophobic frit before concentration in vacuo to give a dark red oil. The crude material was dissolved in MeOH (40 mL) and hydrogenated using the H-Cube (setting: 40° C., full H₂). The crude mixture was concentrated in vacuo, re-dissolved in a minimum amount of DCM and loaded on the top of an aminopropyl silica cartridge (70 g). The column was eluted using a gradient 0-100% EtOAc/cyclohexane over 60 minutes followed by flushing with 0-25% MeOH/DCM. The appropriate fractions were combined and evaporated in vacuo to give an orange oil. The oil was dissolved in methanol (40 mL) and run through the H-cube (setting: full H₂, 40° C., 10% palladium on carbon CatCart30 as the catalyst). The solution was concentrated in vacuo to yield the title compound as pale yellow oil (119 mg).

LCMS (System B): $t_{RET}$=1.19 min; MH⁺ 513

Intermediate 25: (S)-5-Butyl-N-(2,4-dimethoxybenzyl)-3-(5-(3-fluoropyrrolidin-1-yl)pentyl)-1H-pyrazolo[4,3-d]pyrimidin-7-amine Triethylamine (0.860 mL, 6.20 mmol) was added to a mixture of (S)-3-fluoropyrrolidine hydrochloride (390 mg, 3.10 mmol) and 5-butyl-3-(5-chloropent-1-yn-1-yl)-N-(2,4-dimethoxybenzyl)-1H-pyrazolo[4,3-d]pyrimidin-7-amine (457 mg, 1.034 mmol) in N,N-dimethylformamide (7 mL). The mixture was heated to 80° C. and stirred for 18 hours. An additional portion of (S)-3-fluoropyrrolidine hydrochloride (195 mg, 1.55 mmol) and triethylamine (0.430 mL, 3.10 mol) were added to the reaction mixture. The reaction was stirred at 80° C. for a further 6 hours. N,N-Dimethylformamide (3 mL) was added and the reaction mixture was stirred at 80° C. for a further 18 hours and then allowed to cool to room temperature. The mixture was evaporated in-vacuo to yield a brown oil. The resulting oil was partitioned between dichloromethane (50 mL) and water/brine (20 mL). The organic layer was separated, passed through a hydrophobic frit and evaporated in-vacuo to yield a brown oil. The oil was dissolved in the minimum volume of dichloromethane, loaded onto a 50 g aminopropyl functionalised silica cartridge and purified using a 0-10% methanol in dichloromethane gradient over 40 minutes. (detection wavelength=230 nm). Appropriate fractions were combined and evaporated in-vacuo to yield a brown oil (261 mg). A mixture of the oil and 10% palladium on carbon (50 mg) in ethanol (20 mL) was stirred under a hydrogen atmosphere for 3 hours. Additional 10% palladium on carbon (50 mg) was added to the reaction and the mixture was stirred under a hydrogen atmosphere for 18 hours. A further portion of 10% palladium on carbon (50 mg) was added to the reaction and the mixture was stirred under a hydrogen atmosphere for 5 hours. The reaction was filtered through a celite cartridge (10 g) and evaporated in-vacuo to yield a brown oil. The oil was dissolved in the minimum volume of dichloromethane, loaded onto a 50 g aminopropyl functionalised silica cartridge and purified using a 0-10% methanol in dichloromethane gradient over 40 mins. (detection wavelength=230 nm). Appropriate fractions were combined and evaporated in-vacuo to yield the title compound as a brown oil (175 mg).

LCMS (System B): $t_{RET}$=1.23 min; MH⁺ 499

Intermediate 26: (R)-5-Butyl-N-(3,4-dimethoxybenzyl)-3-(6-(3-fluoropyrrolidin-1-yl)hexyl)-1H-pyrazolo[4,3-d]pyrimidin-7-amine Prepared similarly to Intermediate 24 from 5-butyl-3-(6-chlorohex-1-yn-1-yl)-N-(3,4-dimethoxybenzyl)-1H-pyrazolo[4,3-d]pyrimidin-7-amine and (R)-3-fluoropyrrolidine hydrochloride LCMS (System B): $t_{RET}$=1.17 min; MH⁺ 513

Intermediate 27: (R)-5-butyl-N-(2,4-dimethoxybenzyl)-3-(5-(3-fluoropyrrolidin-1-yl)pentyl)-1H-pyrazolo[4,3-d]pyrimidin-7-amine Prepared similarly to Intermediate 25 from and 5-butyl-3-(5-chloropent-1-yn-1-yl)-N-(2,4-dimethoxybenzyl)-1H-pyrazolo[4,3-d]pyrimidin-7-amine and (R)-3-fluoropyrrolidine hydrochloride LCMS (System B): $t_{RET}$=1.23 min; MH⁺ 499

Intermediate 28: 1-(6-(5-Butyl-7-((2,4-dimethoxybenzyl)amino)-1H-pyrazolo[4,3-d]pyrimidin-3-yl)hexyl)piperidin-4-ol Prepared similarly to Intermediate 22 from 5-butyl-3-(6-chlorohex-1-yn-1-yl)-N-(2,4-dimethoxybenzyl)-1H-pyrazolo[4,3-d]pyrimidin-7-amine and 4-hydroxypiperidine LCMS (System B): $t_{RET}$=1.09 min; MH$^+$ 525

Intermediate 29: 1-(5-(5-Butyl-7-((2,4-dimethoxybenzyl)amino)-1H-pyrazolo[4,3-d]pyrimidin-3-yl)pentyl)piperidin-4-ol Triethylamine (0.327 mL, 2.355 mmol) was added to a solution of 4-hydroxypiperidine (238 mg, 2.355 mmol) and 5-butyl-3-(5-chloropent-1-yn-1-yl)-N-(2,4-dimethoxybenzyl)-1H-pyrazolo[4,3-d]pyrimidin-7-amine (347 mg, 0.785 mmol) in anhydrous N,N-Dimethylformamide (5 mL). The solution was heated to 80° C. and stirred for 17 hours. An additional portion of 4-hydroxypiperidine (79 mg, 0.785 mmol) was added to the reaction mixture and stirring was continued at 80° C. for 1 hour. The reaction mixture was evaporated in-vacuo to yield a brown oil. The resulting oil was partitioned between dichloromethane (2×25 mL) and water/brine (1:1, 20 mL). The organic layer was separated, passed through a hydrophobic frit and evaporated in-vacuo to yield a brown oil (643 mg). The oil was dissolved in the minimum volume of dichloromethane, loaded onto a 50 g aminopropyl silica cartridge and purified using a 0-10% methanol in dichloromethane gradient over 40 minutes (detection wavelength=230 nm). Appropriate fractions were combined and evaporated in-vacuo to yield a brown solid, (253 mg). A mixture of the solid and 10% palladium on carbon (100 mg) in ethanol (20 mL) was stirred under a hydrogen atmosphere for 6 hours. An additional portion of 10% palladium on carbon (100 mg) was added to the reaction and the mixture was stirred under hydrogen for a further 16 hours. A further portion of 10% palladium on carbon (50 mg) was added to the reaction and the mixture was stirred under hydrogen for a further 3 hours. The reaction was filtered through a celite cartridge (10 g) and evaporated in-vacuo to yield the title compound as a brown oil (224 mg).

LCMS (System B): $t_{RET}$=1.07 min; MH$^+$ 511

Intermediate 30: 5-Butyl-N-(3,4-dimethoxybenzyl)-3-(6-(4-fluoropiperidin-1-yl)hexyl)-1H-pyrazolo[4,3-d]pyrimidin-7-amine Prepared similarly to Intermediate 24 from 5-butyl-3-(6-chlorohex-1-yn-1-yl)-N-(3,4-dimethoxybenzyl)-1H-pyrazolo[4,3-d]pyrimidin-7-amine and 4-fluoropiperidine hydrochloride LCMS (System B): $t_{RET}$=1.23 min; MH$^+$ 527

Intermediate 31: 5-Butyl-N-(2,4-dimethoxybenzyl)-3-(5-(4-fluoropiperidin-1-yl)pentyl)-1H-pyrazolo[4,3-d]pyrimidin-7-amine Prepared similarly to Intermediate 25 from and 5-butyl-3-(5-chloropent-1-yn-1-yl)-N-(2,4-dimethoxybenzyl)-1H-pyrazolo[4,3-d]pyrimidin-7-amine and 4-fluoropiperidine hydrochloride LCMS (System B): $t_{RET}$=1.26 min; MH$^+$ 513

EXAMPLE PREPARATION

Example 1: 5-Butyl-3-(6-(piperidin-1-yl)hexyl)-1H-pyrazolo[4,3-d]pyrimidin-7-amine formate

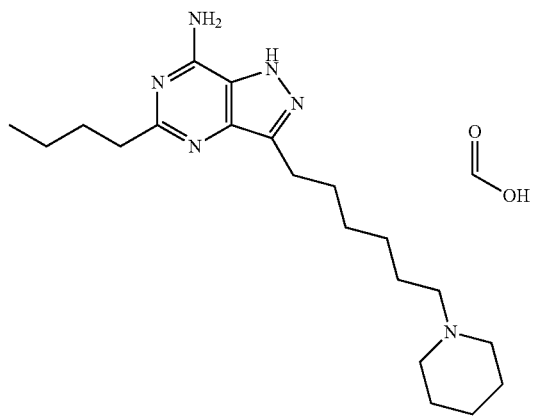 [SMILES: CCCCc1nc(N)c2[nH]nc(CCCCCCN3CCCCC3)c2n1 ; O=CO]

A mixture of 5-butyl-3-(6-(piperidin-1-yl)hexyl)-1H-pyrazolo[4,3-d]pyrimidin-7(6H)-one (87 mg, 0.242 mmol) and phosphorus oxychloride (1.5 mL, 16.09 mmol) was heated at 120° C. for 45 minutes. The reaction was cooled to room temperature and added dropwise with vigorous stirring to 20% aqueous sodium hydroxide solution (24 mL) (pH of mixture after addition was 14). The mixture was adjusted to pH12 using 2M aqueous citric acid solution and extracted into ethyl acetate. The organic layer was separated, passed through a hydrophobic frit and evaporated in-vacuo to yield a red/brown oil (95 mg). The material (95 mg) was suspended in 2-propanol (2 mL) and 35% (0.88) ammonia solution (2 mL). The reaction was stirred at 140° C. for 90 minutes in a Biotage Initiator microwave. Reaction evaporated in-vacuo to yield a red oil. The oil was dissolved in MeOH:DMSO (1:1) (2×1 mL) and purified by MDAP (Method A). The appropriate fractions were combined and evaporated in-vacuo to yield the title compound as a colourless oil (13.2 mg).

LCMS (System A): $t_{RET}$=0.44 min; MH$^+$ 359

Example 2: 5-(2-Methoxyethyl)-3-(6-(piperidin-1-yl)hexyl)-1H-pyrazolo[4,3-d]pyrimidin-7-amine

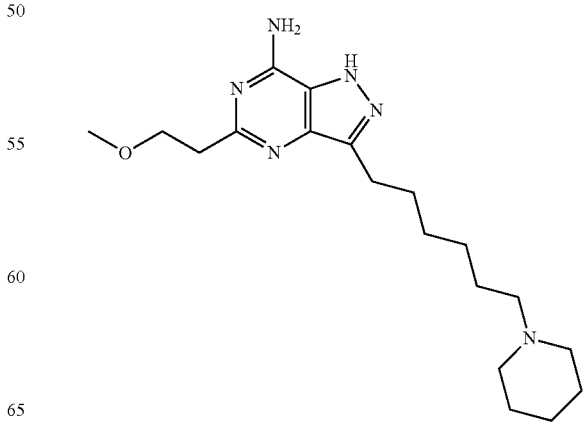

A mixture of 5-(2-methoxyethyl)-3-(6-(piperidin-1-yl)hexyl)-1H-pyrazolo[4,3-d]pyrimidin-7(6H)-one (116.5 mg, 0.322 mmol) and phosphorus oxychloride (1.9 mL, 20.38 mmol) was heated at 120° C. for 45 minutes. The reaction was cooled to room temperature and evaporated in-vacuo to yield a red/brown oil. Toluene (5 mL) was added to the oil and the resulting suspension was evaporated in-vacuo to yield a red/brown oil. The oil was dissolved in iso-propanol (2 mL) and 0.88 ammonia (2 mL, 36.2 mmol) was added. The reaction was stirred at 100° C. for 60 minutes in a Biotage Initiator microwave the the reaction was evaporated in-vacuo to yield a red solid. The oil was dissolved in MeOH:DMSO (1:1) (2×1 mL) and purified by MDAP (Method B). Appropriate fractions were combined and evaporated in-vacuo to yield the title compound as a clear oil (15.6 mg).

LCMS (System B): $t_{RET}$=0.76 min; MH$^+$ 361

Example 3: 5-Butyl-3-(6-(pyrrolidin-1-yl)hexyl)-1H-pyrazolo[4,3-d]pyrimidin-7-amine

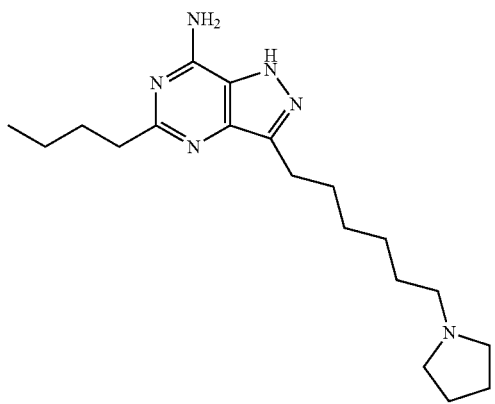 [SMILES: CCCCc1nc(N)c2[nH]nc(CCCCCCN3CCCC3)c2n1]

Method A

A mixture of 5-butyl-3-(6-(pyrrolidin-1-yl)hexyl)-1H-pyrazolo[4,3-d]pyrimidin-7(6H)-one (245 mg, 0.709 mmol) and phosphorus oxychloride (12.89 mL, 138 mmol) was stirred at 120° C. for 45 mins. The reaction was cooled to room temperature and evaporated in-vacuo to yield a red/brown oil. Toluene (10 mL) was added to the oil and the resulting suspension was evaporated in-vacuo to yield a red/brown oil. The oil was dissolved in iso-propanol (7 mL) and 0.88 ammonia (5.88 mL, 106 mmol) was added. The reaction was stirred at 120° C. for 60 minutes in a Biotage Initiator microwave then the reaction evaporated in-vacuo to yield an orange solid. The crude material was purified by reverse phase chromatography using MDAP (Method A). Fractions which contained product were evaporated in-vacuo to yield the title compound as a colourless oil (72.1 mg).

LCMS (System B): $t_{RET}$=0.84 min; MH$^+$ 345

Method B

A mixture of 5-butyl-N-(3,4-dimethoxybenzyl)-3-(6-(pyrrolidin-1-yl)hex-1-yn-1-yl)-1H-pyrazolo[4,3-d]pyrimidin-7-amine (1.838 g, 3.75 mmol) and 10 wt % palladium on carbon (200 mg) in ethanol (53 mL) was stirred under a hydrogen atmosphere at room temperature for 2 hours. A further 300 mg of 10 wt % palladium on carbon was added to the reaction under a nitrogen atmosphere and the reaction was stirred under a hydrogen atmosphere at room temperature for 2 hours. A further 250 mg of 10 wt % palladium on carbon was added to the reaction under a nitrogen atmosphere and the reaction was stirred under a hydrogen atmosphere at room temperature for 16 hours. The reaction mixture was filtered through a 10 g celite cartridge and the filtrate evaporated in-vacuo to yield a sticky brown oil (2.2 g) The oil was dissolved in trifluoroacetic acid (10 mL) and heated in a Biotage Initiator microwave (using initial absorption setting high) to 120° C. for 4 hours then was left at room temperature for 17 hours. The black/very dark green reaction mixture was evaporated in-vacuo and the remaining residue partitioned between 25% 2-propanol in chloroform (500 mL) and 0.1M aqueous sodium hydroxide solution (500 mL). The organic phase was passed through a hydrophobic frit and evaporated in-vacuo to yield a brown gum (1.74 g). The gum was dissolved in the minimum volume of dichloromethane, loaded onto a 100 g dichloromethane pre-conditioned silica cartridge and purified by chromatography using dichloromethane over 1 column volume followed by 0-30% methanol (+1% triethylamine) in dichloromethane gradient over 18 column volumes followed by 30% methanol (+1% triethylamine) in dichloromethane over 6 column volumes (detection wavelength=230 nm). Appropriate fractions were combined and evaporated in-vacuo to yield the title compound as a pale brown solid (596 mg).

LCMS (System A): $t_{RET}$=0.80 min; MH$^+$ 345

Method C 5-butyl-N-(2,4-dimethoxybenzyl)-3-(6-(pyrrolidin-1-yl)hexyl)-1H-pyrazolo[4,3-d]pyrimidin-7-amine (5.33 g, 10.77 mmol) was dissolved in trifluoroacetic acid (45 mL, 584 mmol) at ambient temperature. The reaction mixture was stirred at 60° C. for 3 h. The reaction mixture was evaporated in vacuo and the residue was dissolved in 3:1 chloroform:IPA (500 mL) and washed with dilute (0.2M) aqueous sodium hydroxide (400 mL). The aqueous mixture was extracted with further portions of 3:1 chloroform:IPA (2×400 mL). The combined organic phase was filtered through a hydrophobic frit and the filtrate was evaporated in vacuo to give a yellow solid (4.7 g). A portion of the crude material (1.26 g) was dissolved in dichloromethane/methane (1519:1) and the cloudy solution filtered through a pad of glassfibre filter papers under vacuum. The filtrate was evaporated in vacuo and the residue triturated with ether. The suspension was filtered and the solid material washed with ether to give the title compound as an off-white solid (0.695 g).

LCMS (System B): $t_{RET}$=0.83 min; MH$^+$ 345

$^1$H NMR (400 MHz, METHANOL-$d_4$) δ=3.02-2.92 (m, 6H), 2.87-2.80 (m, 2H), 2.78-2.71 (m, 2H), 1.95 (s, 4H), 1.85-1.71 (m, 4H), 1.68-1.58 (m, 2H), 1.49-1.35 (m, 6H), 0.96 (t, J=7.3 Hz, 3H)

The remainder of the material was dissolved in dichloromethane/methane (50 mL, 19:1) and the cloudy solution filtered through a pad of glassfibre filter papers under vacuum. The filtrate was evaporated in vacuo and the residue triturated with ether. The suspension was filtered and the solid material washed with ether to give a further potion of the title compound as an off-white solid (2.174 g).

LCMS (System B): $t_{RET}$=0.85 min; MH$^+$ 345

Example 4: 5-(2-Methoxyethyl)-3-(6-(pyrrolidin-1-yl)hexyl)-1H-pyrazolo[4,3-d]pyrimidin-7-amine

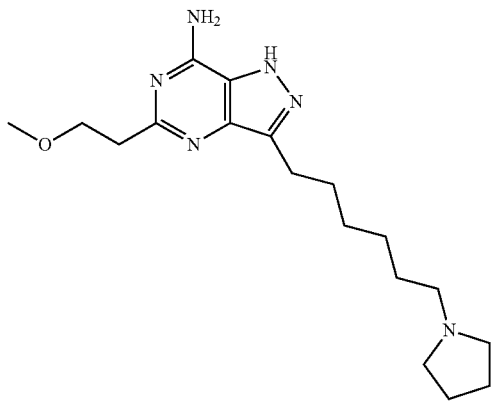 [SMILES: COCCc1nc(N)c2[nH]nc(CCCCCCN3CCCC3)c2n1]

Prepared similarly to Example 2 from 5-(2-methoxyethyl)-3-(6-(pyrrolidin-1-yl)hexyl)-1H-pyrazolo[4,3-d]pyrimidin-7(6H)-one LCMS (System B): $t_{RET}$=0.65 min; MH$^+$ 347

Example 5: 5-Butyl-3-(5-(piperidin-1-yl)pentyl)-1H-pyrazolo[4,3-d]pyrimidin-7-amine

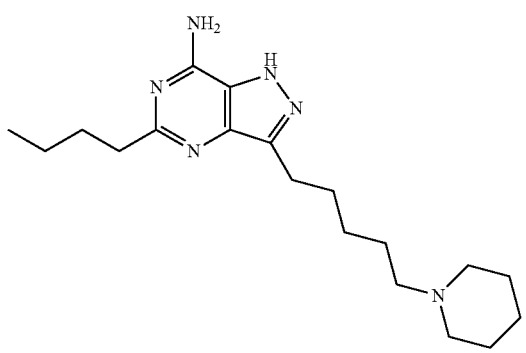 [SMILES: CCCCc1nc(N)c2[nH]nc(CCCCCN3CCCCC3)c2n1]

Prepared similarly to Example 2 from 5-butyl-3-(5-(piperidin-1-yl)pentyl)-1H-pyrazolo[4,3-d]pyrimidin-7(6H)-one.

LCMS (System B): $t_{RET}$=0.84 min; MH$^+$ 345

Example 6: 5-Butyl-3-(5-(pyrrolidin-1-yl)pentyl)-1H-pyrazolo[4,3-d]pyrimidin-7-amine

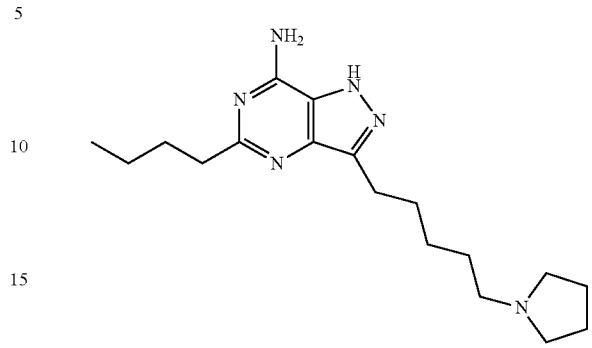

Prepared similarly to Example 2 from 5-butyl-3-(5-(pyrrolidin-1-yl)pentyl)-1H-pyrazolo[4,3-d]pyrimidin-7(6H)-one LCMS (System B): $t_{RET}$=0.84 min; MH$^+$ 345

Example 7: 5-Butyl-3-(7-(piperidin-1-yl)heptyl)-1H-pyrazolo[4,3-d]pyrimidin-7-amine

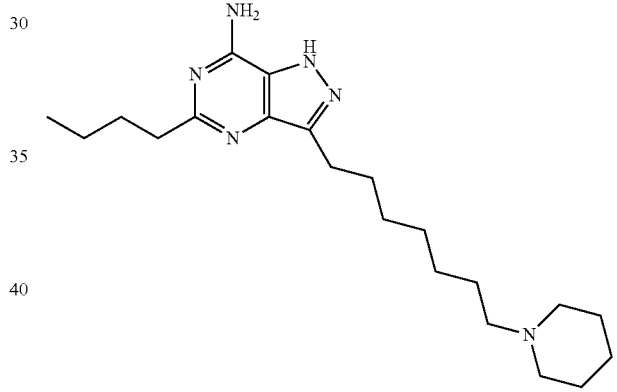

Triethylamine (0.085 mL, 0.608 mmol) was added to a solution of 3-(7-bromoheptyl)-5-butyl-N-(2,4-dimethoxybenzyl)-1H-pyrazolo[4,3-d]pyrimidin-7-amine (150 mg, 0.203 mmol) and piperidine (0.060 mL, 0.608 mmol) in anhydrous acetonitrile (7 mL). The solution was stirred at ambient temperature for 1.5 hours. Additional piperidine (0.060 mL, 0.608 mmol) and triethylamine (0.085 mL, 0.608 mmol) were added to the reaction mixture and stirring at ambient temperature was continued for 17 hours. The reaction mixture was evaporated in vacuo to yield a clear oil. The oil was partitioned between ethyl acetate (20 mL) and water/brine (1:1, 5 mL). The organic layer was separated, passed through a hydrophobic frit and evaporated in vacuo to yield a clear oil. The oil was dissolved in trifluoroacetic acid (3 mL, 38.9 mmol) and heated at 60° C. for 3 hours. The reaction mixture was evaporated in-vacuo and the residue was dissolved in 3:1 chloroform:IPA (20 mL) and washed with aqueous sodium hydroxide (0.1M, 5 mL). The organic phase was separated using a hydrophobic frit and the aqueous back extracted with 3:1 chloroform:IPA (20 mL). The combined organic extracts were evaporated in-vacuo to yield a yellow oil (215 mg). The oil was dissolved in MeOH:DMSO (1:1) (3×1 mL) and purified by MDAP (Method B). Appropriate fractions were combined and evaporated in-vacuo to yield a brown oil (88.2 mg). The oil was dissolved in MeOH:DMSO (1:1) (1 mL) and purified by MDAP (Method A). Appropriate fractions were combined and evaporated in-vacuo to yield the title compound as a white solid (40.5 mg).

LCMS (System B): $t_{RET}$=0.94 min; MH$^+$ 373

Example 8: 5-Butyl-3-(7-(pyrrolidin-1-yl)heptyl)-1H-pyrazolo[4,3-d]pyrimidin-7-amine

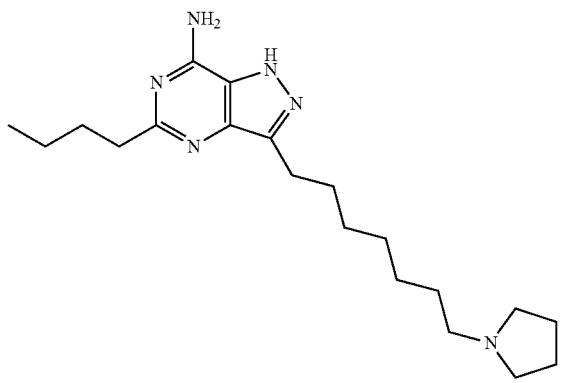 [SMILES: CCCCc1nc(N)c2[nH]nc(CCCCCCCN3CCCC3)c2n1]

Prepared similarly to Example 7 from 3-(7-bromoheptyl)-5-butyl-N-(2,4-dimethoxybenzyl)-1H-pyrazolo[4,3-d]pyrimidin-7-amine and pyrrolidine LCMS (System B): $t_{RET}$=0.82 min; MH$^+$ 359

Example 9: 3-(6-(Azepan-1-yl)hexyl)-5-butyl-1H-pyrazolo[4,3-d]pyrimidin-7-amine

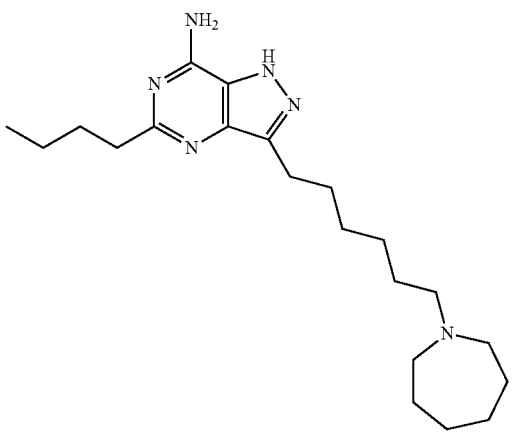 [SMILES: CCCCc1nc(N)c2[nH]nc(CCCCCCN3CCCCCC3)c2n1]

3-(6-(Azepan-1-yl)hexyl)-5-butyl-N-(2,4-dimethoxybenzyl)-1H-pyrazolo[4,3-d]pyrimidin-7-amine (0.100 g, 0.191 mmol) was dissolved in trifluoroacetic acid (2 mL, 26.0 mmol) at ambient temperature. The reaction mixture was stirred at 60° C. for 4 hours. The reaction mixture was evaporated in vacuo and the residue was dissolved in 3:1 chloroform:IPA (15 mL) and washed with aqueous sodium hydroxide (0.1M, 5 mL). The organic phase was separated using a hydrophobic frit and evaporated in vacuo to give a brown oil (0.157 g). The oil was dissolved in MeOH:DMSO (1:1) (2 mL) and purified by MDAP (Method B). Appropriate fractions were combined and evaporated in-vacuo to yield the title compound as an off-white solid (38 mg).

LCMS (System B): $t_{RET}$=0.88 min; MH$^+$ 373

Example 10: 3-(5-(Azepan-1-yl)pentyl)-5-butyl-1H-pyrazolo[4,3-d]pyrimidin-7-amine

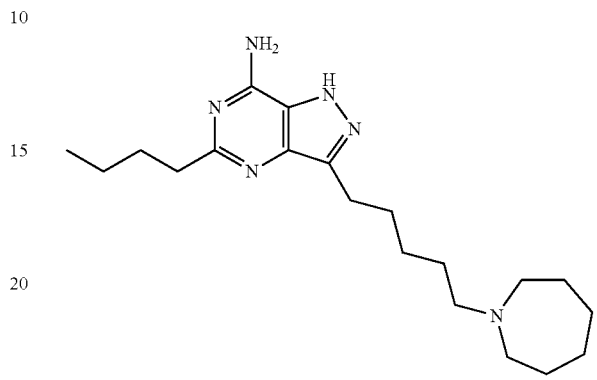

Triethylamine (0.282 mL, 2.036 mmol) was added to a solution of hexamethyleneimine (0.229 mL, 2.036 mmol) and 5-butyl-3-(5-chloropent-1-yn-1-yl)-N-(2,4-dimethoxybenzyl)-1H-pyrazolo[4,3-d]pyrimidin-7-amine (300 mg, 0.679 mmol) in anhydrous N,N-Dimethylformamide (5 mL). The solution was heated to 80° C. and stirred for 3.5 hours. A further 1.5 equivalents of hexamethyleneimine (101 mg, 1.018 mmol) and triethylamine (0.141 mL, 1.018 mmol) in anhydrous N,N-dimethylformamide (2 mL) were added to the reaction mixture and stirring continued at 80° C. for 18 hours.

An additional portion of hexamethyleneimine (101 mg, 1.018 mmol) and triethylamine (0.141 mL, 1.018 mmol) in anhydrous N,N-dimethylformamide (3 mL) was added to the reaction mixture and stirring continued at 80° C. for 5.5 hours. The reaction mixture was evaporated in-vacuo to yield a brown oil. The resulting oil was partitioned between dichloromethane (25 mL) and water/brine (1:1, 20 mL). The organic layer was separated, passed through a hydrophobic frit and evaporated in-vacuo to yield a brown oil. The oil was dissolved in the minimum volume of dichloromethane, loaded onto a 50 g aminopropyl silica cartridge and purified using a 0-10% methanol in dichloromethane gradient over 40 minutes (detection wavelength=230 nm). Appropriate fractions were combined and evaporated in-vacuo to yield a brown oil, (235 mg). The oil was dissolved in the minimum volume of dichloromethane, loaded onto a 50 g aminopropyl silica cartridge and re-purified using a 0-10% methanol in dichloromethane gradient over 40 mins. (detection wavelength=230 nm). Appropriate fractions were combined and evaporated in-vacuo to yield the intermediate alkyne as a brown oil, (195 mg).

A mixture of the oil and 10% palladium on carbon (150 mg) in ethanol (20 mL) was stirred under a hydrogen atmosphere for 19 hours. Additional 10% palladium on carbon (100 mg) was added to the reaction and the mixture was stirred under a hydrogen atmosphere for a further 23 hours. Additional 10% palladium on carbon (100 mg) was added to the reaction and the mixture was stirred under a hydrogen atmosphere for a further 5 hours. The reaction was filtered through a celite cartridge (10 g) and evaporated in-vacuo to yield as a brown oil (180 mg). The oil was dissolved in MeOH:DMSO (1:1) (3 mL) and purified by MDAP (Method B). Appropriate fractions were combined and evaporated in-vacuo to yield a yellow oil. The oil was dissolved in trifluoroacetic acid (3 mL, 38.9 mmol) and heated at 60° C. for 3 hours. The reaction was stirred at 60° C. for a further 2 hours and then allowed to cool to room temperature over night. The reaction mixture was evaporated in-vacuo and the residue was dissolved in 3:1 chloroform:IPA (15 mL) and washed with aqueous sodium hydroxide (0.1M, 6 mL). The organic phase was separated using a hydrophobic frit and the aqueous back extracted with 3:1 chloroform:IPA (15 mL). The combined organic extracts were evaporated in-vacuo to yield a brown oil. The oil was dissolved in MeOH:DMSO (1:1) (3 mL) and purified by MDAP (Method B). Appropriate fractions were combined and evaporated in-vacuo to yield the title compound as an pale beige solid (32 mg).

LCMS (System B): $t_{RET}$=0.79 min; MH$^+$ 359

Example 11: (S)-5-Butyl-3-(6-(3-fluoropyrrolidin-1-yl)hexyl)-1H-pyrazolo[4,3-d]pyrimidin-7-amine

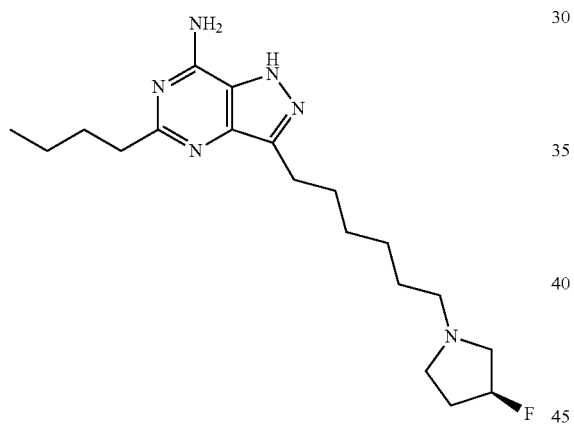

A solution of (S)-5-butyl-N-(3,4-dimethoxybenzyl)-3-(6-(3-fluoropyrrolidin-1-yl)hexyl)-1H-pyrazolo[4,3-d]pyrimidin-7-amine (119 mg, 0.232 mmol) in trifluoroacetic acid (1 mL, 12.98 mmol) was heated in a Biotage Initiator microwave (using initial absorption setting high) at 120° C. for 2.5 h. The reaction mixture was concentrated in vacuo and the residue was dissolved in 3:1 chloroform:IPA (50 mL) and washed with aqueous sodium hydroxide (0.1M, 50 mL). The organic phase was separated and the aqueous back extracted with 3:1 chloroform:IPA (30 mL). The combined organic extracts were dried (hydrophobic frit) and concentrated in vacuo. The material (223 mg) was dissolved in MeOH:DMSO (1:1) (2 mL) and purified by MDAP (Method B). Appropriate fractions were combined and evaporated in-vacuo to yield the title compound as an orange solid (33 mg).

LCMS (System B): $t_{RET}$=0.91 min; MH$^+$ 363

Example 12: (S)-5-Butyl-3-(5-(3-fluoropyrrolidin-1-yl)pentyl)-1H-pyrazolo[4,3-d]pyrimidin-7-amine

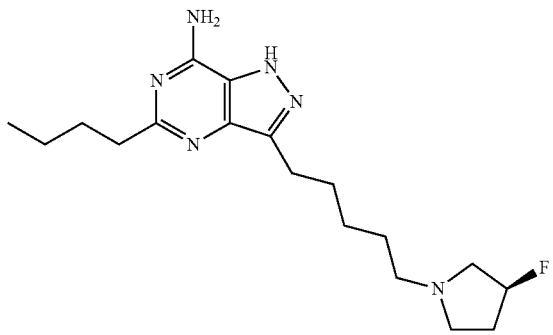 [SMILES: CCCCc1nc(N)c2[nH]nc(CCCCCN3CC[C@H](F)C3)c2n1]

Prepared similarly to Example 9 from (S)-5-butyl-N-(2,4-dimethoxybenzyl)-3-(5-(3-fluoropyrrolidin-1-yl)pentyl)-1H-pyrazolo[4,3-d]pyrimidin-7-amine LCMS (System B): $t_{RET}$=0.85 min; MH$^+$ 349

Example 13: (R)-5-Butyl-3-(6-(3-fluoropyrrolidin-1-yl)hexyl)-1H-pyrazolo[4,3-d]pyrimidin-7-amine formate

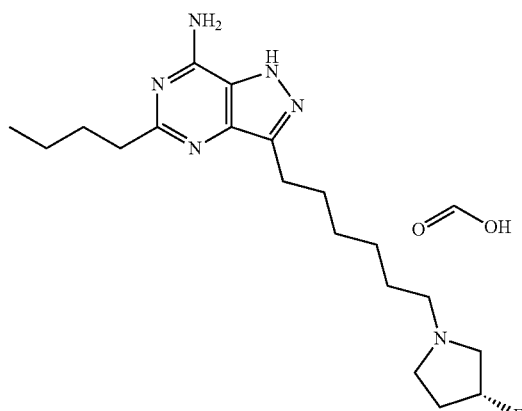

Prepared similarly to Example 11 from (R)-5-butyl-N-(3,4-dimethoxybenzyl)-3-(6-(3-fluoropyrrolidin-1-yl)hexyl)-1H-pyrazolo[4,3-d]pyrimidin-7-amine LCMS (System B): $t_{RET}$=0.88 min; MH$^+$ 363

Example 14: (R)-5-Butyl-3-(5-(3-fluoropyrrolidin-1-yl)pentyl)-1H-pyrazolo[4,3-d]pyrimidin-7-amine Example 16: 1-(5-(7-Amino-5-butyl-1H-pyrazolo[4,3-d]pyrimidin-3-yl)pentyl)piperidin-4-ol

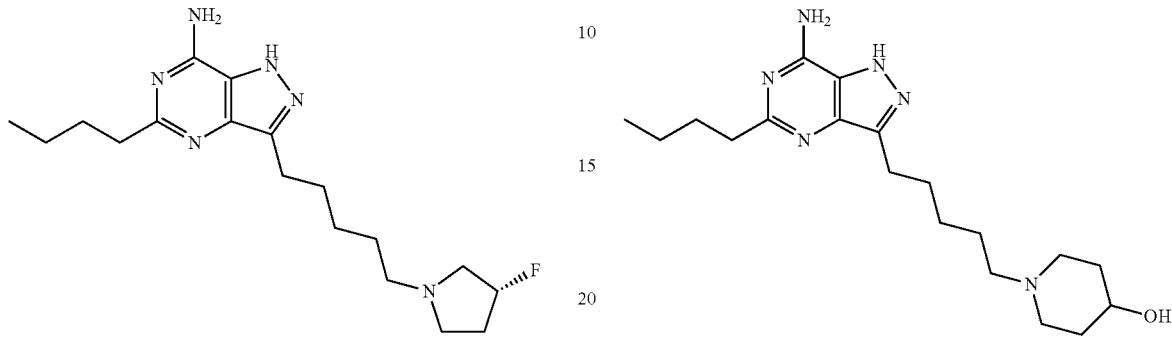

Prepared similarly to Example 9 from (R)-5-butyl-N-(2,4-dimethoxybenzyl)-3-(5-(3-fluoropyrrolidin-1-yl)pentyl)-1H-pyrazolo[4,3-d]pyrimidin-7-amine LCMS (System B): $t_{RET}$=0.85 min; MH$^+$ 349

Example 15: 1-(6-(7-Amino-5-butyl-1H-pyrazolo[4,3-d]pyrimidin-3-yl)hexyl)piperidin-4-ol Prepared similarly to Example 9 from 1-(5-(5-butyl-7-((2,4-dimethoxybenzyl)amino)-1H-pyrazolo[4,3-d]pyrimidin-3-yl)pentyl)piperidin-4-ol LCMS (System B): $t_{RET}$=0.71 min; MH$^+$ 361

Example 17: 5-Butyl-3-(6-(4-fluoropiperidin-1-yl)hexyl)-1H-pyrazolo[4,3-d]pyrimidin-7-amine formate

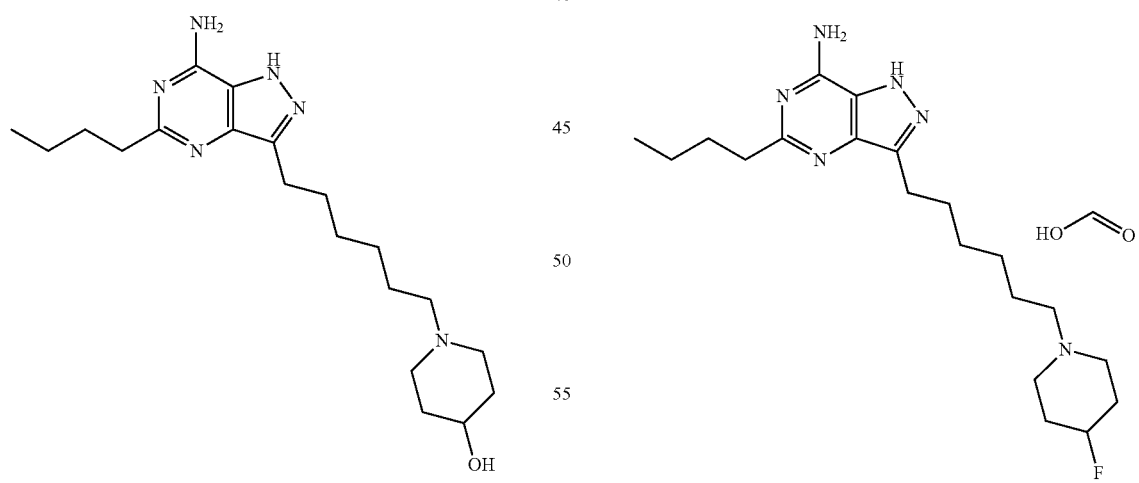

Prepared similarly to Example 9 from 1-(6-(5-butyl-7-((2,4-dimethoxybenzyl)amino)-1H-pyrazolo[4,3-d]pyrimidin-3-yl)hexyl)piperidin-4-ol LCMS (System B): $t_{RET}$=0.76 min; MH$^+$ 375

Prepared similarly to Example 11 from 5-butyl-N-(3,4-dimethoxybenzyl)-3-(6-(4-fluoropiperidin-1-yl)hexyl)-1H-pyrazolo[4,3-d]pyrimidin-7-amine LCMS (System B): $t_{RET}$=0.93 min; MH$^+$ 377

Example 18: 5-Butyl-3-(5-(4-fluoropiperidin-1-yl)pentyl)-1H-pyrazolo[4,3-d]pyrimidin-7-amine

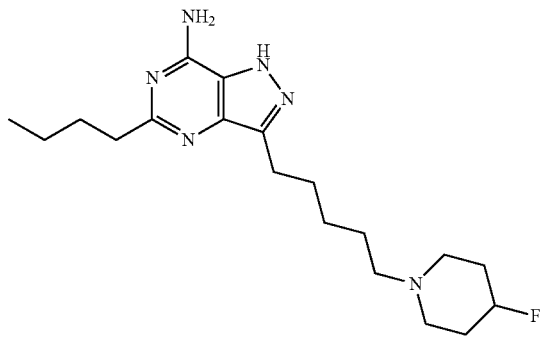 [SMILES: CCCCc1nc(N)c2[nH]nc(CCCCCN3CCC(F)CC3)c2n1]

Prepared similarly to Example 9 from 5-butyl-N-(2,4-dimethoxybenzyl)-3-(5-(4-fluoropiperidin-1-yl)pentyl)-1H-pyrazolo[4,3-d]pyrimidin-7-amine LCMS (System B): $t_{RET}$=0.90 min; MH$^+$ 363

Example 19: 5-Butyl-3-(6-(pyrrolidin-1-yl)hexyl)-1H-pyrazolo[4,3-d]pyrimidin-7-amine maleate

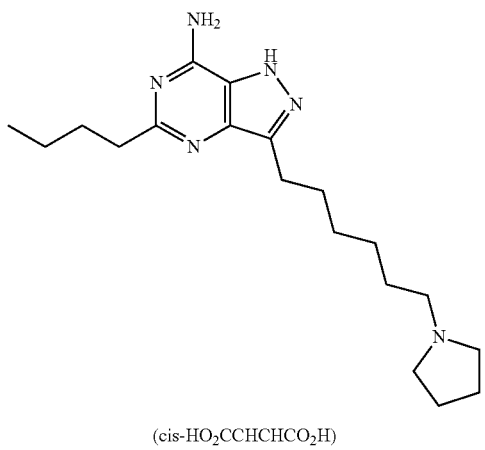 [SMILES: CCCCc1nc(N)c2[nH]nc(CCCCCCN3CCCC3)c2n1]

(cis-HO$_2$CCHCHCO$_2$H)

A round bottomed flask charged with 5-butyl-3-(6-(pyrrolidin-1-yl)hexyl)-1H-pyrazolo[4,3-d]pyrimidin-7-amine (140 mg, 0.406 mmol) was treated with IPA (1.4 mL, 10 vol) and stirred under a nitrogen atmosphere at 50° C. until a homogeneous solution was generated. Maleic acid (47.2 mg, 0.406 mmol) was added directly as a solid and the resulting reaction mixture stirred till complete dissolution of maleic acid had occurred. The resulting solution was then treated with a sonicated slurry of 5-butyl-3-(6-(pyrrolidin-1-yl)hexyl)-1H-pyrazolo[4,3-d]pyrimidin-7-amine maleate (0.5 mg) in IPA (0.1 mL) and the resulting slurry was aged at 50° C. for 1 hour before being allowed to cool to 20° C. over 4 hours. The resulting slurry was then stirred overnight at 20° C. The slurry was cooled to 3° C. in an ice bath and aged for 30 minutes prior to the solid being collected via vacuum filtration. The resulting solid was washed with chilled IPA (2×1 mL) before being oven dried at 40° C. in vacuo overnight to yield an off white solid (122 mg). The resulting solid was further dried in vacuo at 40° C. to afford the title compound as an off-white solid (95 mg).

LCMS (System B): $t_{RET}$=0.79 min; MH$^+$ 345

$^1$H NMR (400 MHz, DMSO-d$_6$) includes δ=7.05 (br. s, 2H), 6.02 (s, 2H), 3.13-3.00 (m, 3H), 2.83 (br. s., 2H), 2.64 (br. s., 2H), 2.03-1.83 (m, 4H), 1.80-1.53 (m, 6H), 1.43-1.25 (m, 6H), 0.90 (t, J=7.5 Hz, 3H)

Example 20: 5-Butyl-3-(6-(pyrrolidin-1-yl)hexyl)-1H-pyrazolo[4,3-d]pyrimidin-7-amine hemimaleate

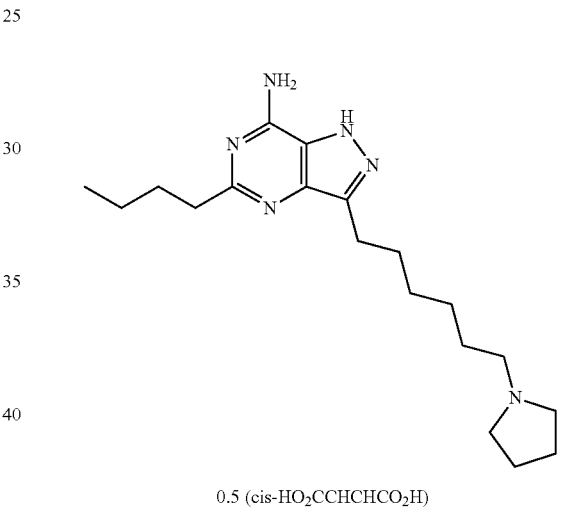

0.5 (cis-HO$_2$CCHCHCO$_2$H)

5-Butyl-3-(6-(pyrrolidin-1-yl)hexyl)-1H-pyrazolo[4,3-d]pyrimidin-7-amine (205 mg,) was treated with maleic acid (34.5 mg, 0.5 eq) before being slurried in IPA (2.0 mL). The resulting reaction mixture was heated to 70° C. resulting in a homogeneous solution which on aging at 70° C. started to precipitate solid. The resulting slurry was found to set solid after 30 mins at 70° C. therefore additional IPA (0.5 mL) was added to mobilise the slurry. The resulting reaction mixture was allowed to cool to 20° C. and was aged overnight at 20° C. before being filtered and washed with fresh IPA (2×4 mL) to yield a white solid which was oven dried at 40° C. in vacuo (90 mbar) overnight. The resulting solid (199 mg) was further dried in vacuo at 50° C. to afford the title compound.

$^1$H NMR (400 MHz, DMSO-d$_6$) includes δ=7.05 (br. s, 2H), 6.01 (s, 1H), 1.89-1.61 (m, 8H), 1.56-1.43 (m, 2H), 1.41-1.24 (m, 6H), 0.89 (t, J=7.4 Hz, 3H)

Example 21: 5-Butyl-3-(6-(pyrrolidin-1-yl)hexyl)-1H-pyrazolo[4,3-d]pyrimidin-7-amine dimaleate

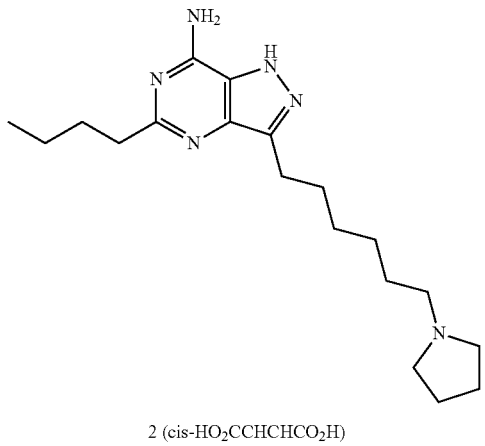 [SMILES: CCCCc1nc(N)c2[nH]nc(CCCCCCN3CCCC3)c2n1]

2 (cis-HO$_2$CCHCHCO$_2$H)

5-Butyl-3-(6-(pyrrolidin-1-yl)hexyl)-1H-pyrazolo[4,3-d]pyrimidin-7-amine (197.3 mg,) was treated with maleic acid (133 mg, 2.0 eq) before being slurried in IPA (2.0 mL). The resulting reaction mixture was heated to 70° C. resulting in a homogeneous solution which on aging at 70° C. started to precipitate solid. The resulting slurry was found to set solid at 70° C. therefore an additional IPA (2.0 mL) was added to mobilise the slurry. The resulting reaction mixture was allowed to cool slowly to 20° C. and was aged overnight at 20° C. before being filtered and washed with fresh IPA (2×4 mL) to yield a white solid which was oven dried at 40° C. in vacuo (90 mbar) overnight to afford the title compound (294 mg).

$^1$H NMR (400 MHz, DMSO-d$_6$) includes δ=6.07 (s, 4H), 3.15-3.03 (m, 2H), 2.80-2.64 (m, 2H), 2.09-1.51 (m, J=7.9 Hz, 10H), 1.42-1.25 (m, 6H), 0.91 (t, J=7.4 Hz, 3H)

Example 22: 5-Butyl-3-(6-(pyrrolidin-1-yl)hexyl)-1H-pyrazolo[4,3-d]pyrimidin-7-amine hemi-succinate

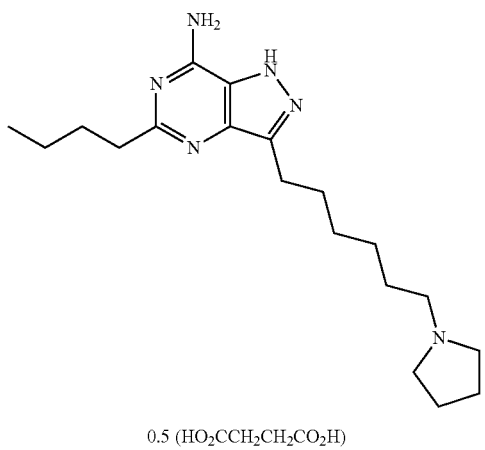 [SMILES: CCCCc1nc(N)c2[nH]nc(CCCCCCN3CCCC3)c2n1]

0.5 (HO$_2$CCH$_2$CH$_2$CO$_2$H)

5-Butyl-3-(6-(pyrrolidin-1-yl)hexyl)-1H-pyrazolo[4,3-d]pyrimidin-7-amine (196.7 mg,) was treated with succinic acid (33.7 mg, 0.5 eq) before being slurried in IPA (2.0 mL). The resulting reaction mixture was heated to 70° C. resulting in a homogeneous solution which on aging at 70° C. started to precipitate solid. The resulting slurry was found to set solid at 70° C. therefore additional IPA (1.0 mL) was added to mobilise the slurry. The resulting reaction mixture was allowed to cool slowly to 20° C. and was aged overnight at 20° C. before being filtered and washed with fresh IPA (2×4 mL) to yield a white solid which was oven dried at 40° C. in vacuo (90 mbar) overnight. The resulting solid (193 mg) was further dried in vacuo at 50° C. to afford the title compound.

$^1$H NMR (400 MHz, DMSO-d$_6$) includes δ=7.08 (br. s., 2H), 2.88-2.75 (m, 2H), 2.32 (s, 2H), 1.80-1.59 (m, 8H), 1.53-1.22 (m, 8H), 0.89 (t, J=7.4 Hz, 3H)

Example 23: 5-Butyl-3-(6-(pyrrolidin-1-yl)hexyl)-1H-pyrazolo[4,3-d]pyrimidin-7-amine methanesulfonate

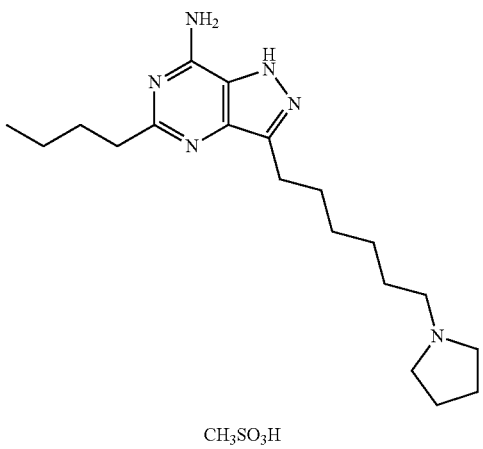 [SMILES: CCCCc1nc(N)c2[nH]nc(CCCCCCN3CCCC3)c2n1 ; "CH3SO3H"]

CH$_3$SO$_3$H

5-Butyl-3-(6-(pyrrolidin-1-yl)hexyl)-1H-pyrazolo[4,3-d]pyrimidin-7-amine (200.3 mg,) slurried in acetonitrile (2 mL) at 70° C. was treated with anhydrous methane sulfonic acid (38 ul, 1.0 eq). The resulting reaction mixture turned over to a solution on addition of methane sulfonic acid and on aging at 70° C. started to precipitate solid. The resulting slurry was found to set solid and therefore additional acetonitrile (2 mL) was added to mobilise the slurry. The resulting reaction mixture was allowed to cool to 20° C. and was aged overnight at 20° C. before being filtered and washed with fresh acetonitrile (2×4 mL) to yield a white solid which was oven dried at 40° C. in vacuo (90 mbar) overnight to afford the title compound (234 mg).

$^1$H NMR (400 MHz, DMSO-d$_6$) includes δ=7.17-6.94 (m, 2H), 2.89-2.76 (m, 2H), 2.64 (br. s., 2H), 2.32 (s, 3H), 1.68 (s, 6H), 1.43-1.23 (m, 6H), 0.90 (t, J=7.4 Hz, 3H)

Example 24: 5-Butyl-3-(6-(pyrrolidin-1-yl)hexyl)-1H-pyrazolo[4,3-d]pyrimidin-7-amine hydrochloride

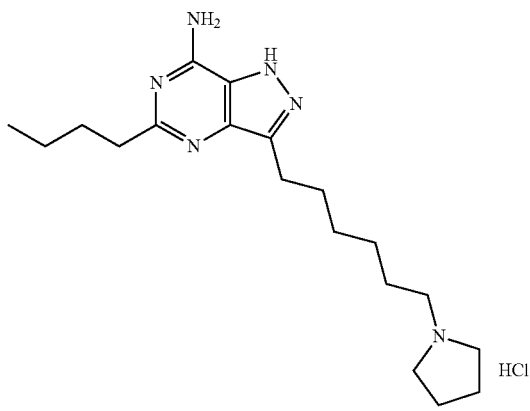 [SMILES: CCCCc1nc(N)c2[nH]nc(CCCCCCN3CCCC3)c2n1 ; Cl]

5-Butyl-3-(6-(pyrrolidin-1-yl)hexyl)-1H-pyrazolo[4,3-d]pyrimidin-7-amine (197.2 mg) was slurried in acetonitrile (2 mL) at 70° C. before treated with 1.25M HCl in IPA (0.458 mL) which generated a solution. On aging at 70° C. the reaction started to precipitate a solid and this stayed mobile throughout age at 70° C. and therefore the reaction was cooled to 20° C. The resulting slurry was aged overnight at 20° C. before being filtered and washed with fresh acetonitrile (2×4 mL) to yield a white solid which was oven dried at 40° C. in vacuo (90 mbar) overnight. The resulting solid (144 mg) was further dried in vacuo at 50° C. to afford the title compound.

$^1$H NMR (400 MHz, DMSO-$d_6$) includes δ=7.18 (br. s, 2H), 2.72-2.57 (m, 2H), 2.04-1.54 (m, 10H), 1.42-1.23 (m, 6H), 0.90 (t, J=7.4 Hz, 3H)

Polymorphism

X-Ray Powder Diffraction (XRPD) was performed on 5-butyl-3-(6-(pyrrolidin-1-yl)hexyl)-1H-pyrazolo[4,3-d]pyrimidin-7-amine according to the following methods.

XRPD

The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

Characteristic XRPD angles and d-spacings for batches are recorded in Table 1 for Examples 21 and 22. The margin of error is approximately ±0.1° 2θ for each of the peak assignments. Peak intensities may vary from sample to sample due to preferred orientation.

Peak positions were measured using Highscore software.

TABLE 1

Characteristic XRPD Peak Positions for Examples 21 and 22

| Example 21 | | Example 22 | |
|---|---|---|---|
| 2θ/° | d-spacings/Å | 2θ/° | d-spacings/Å |
| 5.3 | 16.8 | 8.1 | 10.9 |
| 5.8 | 15.2 | 9.8 | 9.1 |

TABLE 1-continued

Characteristic XRPD Peak Positions for Examples 21 and 22

| Example 21 | | Example 22 | |
|---|---|---|---|
| 2θ/° | d-spacings/Å | 2θ/° | d-spacings/Å |
| 6.4 | 13.9 | 11.6 | 7.6 |
| 9.0 | 9.8 | 16.0 | 5.5 |
| 10.1 | 8.8 | 17.5 | 5.1 |
| 10.9 | 8.1 | 19.5 | 4.5 |
| 11.6 | 7.7 | 20.2 | 4.4 |
| 12.7 | 7.0 | 23.0 | 3.9 |
| 16.0 | 5.5 | 23.7 | 3.7 |
| 19.1 | 4.7 | | |

Representative XRPD Diffractograms are Shown in FIG. 1 and FIG. 2.

BIOLOGICAL EVALUATION

Compounds of the invention were tested for in vitro biological activity in accordance with the following assay.

Assay for the Induction of Interferon-α and TNF-α using Fresh Human Whole Blood (WB)

Compound Preparation

Compounds were prepared at 100× required concentration in DMSO in flat-bottom microtitre plates at a volume of 1.5 μL. Columns 1-10 contained a 1 in 4 serial dilution of the test compound. Included on each plate was a serial dilution of the TLR7/8 agonist resiquimod as a standard and Column 11 contained 1.5 μl of 200 μM resiquimod (giving a 2 μM final concentration, used to define the approximate maximal response to resiquimod). Each compound was assayed in duplicate for each donor.

Incubation and Assays for Interferon-α and TNF-α

Blood samples from three human donors were collected into sodium heparin (10 U/ml). 150 μl of whole Blood was dispensed into Col 1 to 11 of assay plates containing 1.5 μl of test compound or standard in DMSO. Plates were placed in an incubator overnight (37° C., 95% air, 5% $CO_2$). Following the overnight incubation, plates were removed from the incubator & mixed on an orbital shaker for approximately 1 minute. 100 μl of 0.9% saline was added to each well and the plates mixed again on an orbital shaker. Plates were then centrifuged (2500 rpm, 10 mins), after which a sample of plasma was removed using a Biomek FX and assayed for both IFN-α and TNF-α using the MSD (Mesoscale Discovery) electrochemiluminescence assay platform. The IFN-α assay was carried out similarly to that described above. The TNF-α assay was carried out as per kit instructions (Cat No K111BHB).

Cytokine released was expressed as a percentage of the 2 μM resiquimod control (column 11). This percentage was plotted against compound concentration and the $pEC_{50}$ for the response determined by non-linear least squares curve fitting. For the IFN-α responses, generally a 4 parameter logistic model was selected. For the TNF responses where a clear maximum response was obtained (i.e. a well defined plateau in the response was observed) then a 4 parameter model was generally used. If the upper asymptote of the curve wasn't well defined then the curve fitting was generally constrained to a maximal response of 100% (i.e. to the response to 2 μM resiquimod) or to the response of the highest concentration tested if this was greater than the resiquimod response. Some curves were bell shaped for one or both cytokines and the cytokine data on the down slope of the bell shaped response (i.e. concentrations above those giving the maximal response) were generally excluded from the fit, usually with the exception of the concentration immediately above the peak response. Curve fitting thus concentrated on the up slope of the dose response curve.

Results

Examples 1 to 24 had a mean $pEC_{50}$ for IFNα of ≥5.9. Examples 3, 21 and 22 had mean $pEC_{50}$ for IFNα of 6.9, 7.2 and 7.6 respectively.

Examples 1 to 24 had a mean $pEC_{50}$ for TNF-α of ≤5.4. Examples 3, 21 and 22 had mean $pEC_{50}$ for THF-α of 4.7, <4.3 and 4.7 respectively.

The invention claimed is:

1. A vaccine composition comprising an antigen or antigen composition, and a compound of formula (I) or a salt thereof:

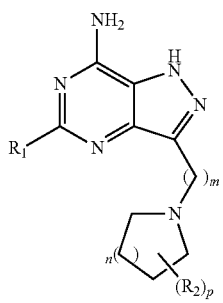

wherein:
$R_1$ is n-$C_{3-6}$alkyl or $C_{1-2}$alkoxy$C_{1-2}$alkyl-;
each $R_2$ independently represents halo, OH or $C_{1-3}$alkyl;
m is an integer having a value of 4, 5, 6 or 7;
n is an integer having a value of 0, 1, 2 or 3;
p is an integer having a value of 0, 1 or 2.

2. The vaccine composition according to claim 1 wherein $R_1$ is n-butyl.

3. The vaccine composition according to claim 1 wherein $R_1$ is 2-methoxyethyl.

4. The vaccine composition according to claim 1 wherein m is an integer having a value of 5 or 6.

5. The vaccine composition according to claim 1 wherein n is 1.

6. The vaccine composition according to claim 1 wherein n is 2.

7. The vaccine composition according to claim 1 wherein p is 0 or 1.

8. The vaccine composition according to claim 1 wherein each $R_2$ independently represents halo or OH.

9. The vaccine composition according to claim 1 wherein each $R_2$ independently represents F or OH.

10. The vaccine composition according to claim 1 wherein the compound is selected from the group consisting of:

5-Butyl-3-(6-(piperidin-1-yl)hexyl)-1H-pyrazolo[4,3-d]pyrimidin-7-amine;
5-(2-Methoxyethyl)-3-(6-(piperidin-1-yl)hexyl)-1H-pyrazolo[4,3-d]pyrimidin-7-amine;
5-Butyl-3-(6-(pyrrolidin-1-yl)hexyl)-1H-pyrazolo[4,3-d]pyrimidin-7-amine;
5-(2-Methoxyethyl)-3-(6-(pyrrolidin-1-yl)hexyl)-1H-pyrazolo[4,3-d]pyrimidin-7-amine;
5-Butyl-3-(5-(piperidin-1-yl)pentyl)-1H-pyrazolo[4,3-d]pyrimidin-7-amine;
5-Butyl-3-(5-(pyrrolidin-1-yl)pentyl)-1H-pyrazolo[4,3-d]pyrimidin-7-amine;
5-Butyl-3-(7-(piperidin-1-yl)heptyl)-1H-pyrazolo[4,3-d]pyrimidin-7-amine;
5-Butyl-3-(7-(pyrrolidin-1-yl)heptyl)-1H-pyrazolo[4,3-d]pyrimidin-7-amine;
3-(6-(Azepan-1-yl)hexyl)-5-butyl-1H-pyrazolo[4,3-d]pyrimidin-7-amine;
3-(5-(Azepan-1-yl)pentyl)-5-butyl-1H-pyrazolo[4,3-d]pyrimidin-7-amine;
(S)-5-Butyl-3-(6-(3-fluoropyrrolidin-1-yl)hexyl)-1H-pyrazolo[4,3-d]pyrimidin-7-amine;
(S)-5-Butyl-3-(5-(3-fluoropyrrolidin-1-yl)pentyl)-1H-pyrazolo[4,3-d]pyrimidin-7-amine;
(R)-5-Butyl-3-(6-(3-fluoropyrrolidin-1-yl)hexyl)-1H-pyrazolo[4,3-d]pyrimidin-7-amine formate;
(R)-5-Butyl-3-(5-(3-fluoropyrrolidin-1-yl)pentyl)-1H-pyrazolo[4,3-d]pyrimidin-7-amine;
1-(6-(7-Amino-5-butyl-1H-pyrazolo[4,3-d]pyrimidin-3-yl)hexyl)piperidin-4-ol;
1-(5-(7-Amino-5-butyl-1H-pyrazolo[4,3-d]pyrimidin-3-yl)pentyl)piperidin-4-ol;
5-Butyl-3-(6-(4-fluoropiperidin-1-yl)hexyl)-1H-pyrazolo[4,3-d]pyrimidin-7-amine; and
5-Butyl-3-(5-(4-fluoropiperidin-1-yl)pentyl)-1H-pyrazolo[4,3-d]pyrimidin-7-amine.

11. The vaccine composition according to claim 1 wherein the compound is 5-Butyl-3-(6-(pyrrolidin-1-yl)hexyl)-1H-pyrazolo[4,3-d]pyrimidin-7-amine, of formula:

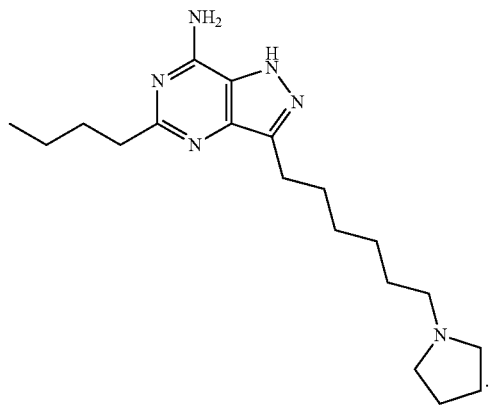 [SMILES: CCCCc1nc(N)c2[nH]nc(CCCCCCN3CCCC3)c2n1]

12. The vaccine composition according to claim 1 wherein the compound is in the form of a pharmaceutically acceptable salt.

13. The vaccine composition according to claim 1 wherein the compound is in the form of a free base.

14. A vaccine composition comprising an antigen or antigen composition, and 5-Butyl-3-(6-(pyrrolidin-1-yl)hexyl)-1H-pyrazolo[4,3-d]pyrimidin-7-amine, of formula:

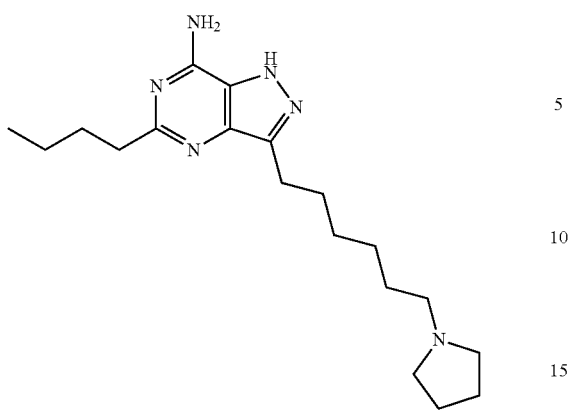
or a salt thereof.
15. The vaccine composition according to claim 14 wherein the compound is in the form of a pharmaceutically acceptable salt.
16. The vaccine composition according to claim 14 wherein the compound is in the form of a free base.
* * * * *